United States Patent
Nakahara et al.

(10) Patent No.: US 7,049,366 B2
(45) Date of Patent: May 23, 2006

(54) ACRYLIC ACID COMPOSITION AND ITS PRODUCTION PROCESS, AND PROCESS FOR PRODUCING WATER-ABSORBENT RESIN USING THIS ACRYLIC ACID COMPOSITION, AND WATER-ABSORBENT RESIN

(75) Inventors: Sei Nakahara, Himeji (JP); Kunihiko Ishizaki, Suita (JP); Hirotama Fujimaru, Himeji (JP); Yasuhisa Nakashima, Himeji (JP); Kazuhiko Sakamoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/472,039

(22) PCT Filed: Dec. 17, 2002

(86) PCT No.: PCT/JP02/13161

§ 371 (c)(1),
(2), (4) Date: Sep. 16, 2003

(87) PCT Pub. No.: WO03/051940

PCT Pub. Date: Jun. 26, 2003

(65) Prior Publication Data

US 2004/0110914 A1   Jun. 10, 2004

(30) Foreign Application Priority Data

Dec. 19, 2001   (JP) ............................. 2001-385746

(51) Int. Cl.
*C08F 120/06*   (2006.01)

(52) U.S. Cl. ...................... 524/556; 526/77; 526/317.1; 526/318.5

(58) Field of Classification Search ............. 526/317.1, 526/77, 318.5; 524/566, 556; 562/600; 528/502

See application file for complete search history.

(56) References Cited

U.S. PATENT DOCUMENTS

| | | | |
|---|---|---|---|
| 3,621,664 A | 11/1971 | Saxer | |
| 3,798,171 A * | 3/1974 | Ishii et al. ............. | 252/182.18 |
| 4,093,776 A | 6/1978 | Aoki et al. | |
| 4,286,082 A | 8/1981 | Tsubakimoto et al. | |
| 4,367,323 A | 1/1983 | Kitamura et al. | |
| 4,446,261 A | 5/1984 | Yamasaki et al. | |
| 4,622,356 A * | 11/1986 | Jarovitzky et al. .......... | 524/100 |
| 4,625,001 A | 11/1986 | Tsubakimoto et al. | |
| 4,654,039 A | 3/1987 | Brandt et al. | |
| 4,683,274 A | 7/1987 | Nakamura et al. | |
| 4,873,299 A | 10/1989 | Nowakowsky et al. | |
| 4,973,632 A | 11/1990 | Nagasuna et al. | |
| 4,985,518 A | 1/1991 | Alexander et al. | |
| 5,061,259 A | 10/1991 | Goldman et al. | |
| 5,124,416 A | 6/1992 | Haruna et al. | |
| 5,145,906 A | 9/1992 | Chambers et al. | |
| 5,244,735 A | 9/1993 | Kimura et al. | |
| 5,250,640 A | 10/1993 | Irie et al. | |
| 5,264,495 A | 11/1993 | Irie et al. | |
| 5,338,810 A | 8/1994 | Shimomura et al. | |
| 5,371,280 A * | 12/1994 | Haramaki et al. ............. | 562/26 |
| 5,380,808 A | 1/1995 | Sumiya et al. | |
| 5,385,983 A | 1/1995 | Graham | |
| 5,409,771 A | 4/1995 | Dahmen et al. | |
| 5,447,727 A | 9/1995 | Graham | |
| 5,462,972 A | 10/1995 | Smith et al. | |
| 5,562,646 A | 10/1996 | Goldman et al. | |
| 5,574,121 A | 11/1996 | Irie et al. | |
| 5,597,873 A | 1/1997 | Chambers et al. | |
| 5,610,220 A | 3/1997 | Klimmek et al. | |
| 5,633,316 A | 5/1997 | Gartner et al. | |
| 5,672,633 A | 9/1997 | Brehm et al. | |
| 5,779,358 A * | 7/1998 | Bevington .................. | 366/206 |
| 5,837,789 A | 11/1998 | Stockhausen et al. | |
| 5,849,405 A | 12/1998 | Wang et al. | |
| 5,851,672 A | 12/1998 | Wang et al. | |
| 6,071,976 A | 6/2000 | Dairoku et al. | |
| 6,139,742 A * | 10/2000 | Bhattacharyya et al. . | 210/500.3 |
| 6,228,930 B1 | 5/2001 | Dairoku et al. | |
| 6,254,990 B1 | 7/2001 | Ishizaki et al. | |
| 6,359,049 B1 | 3/2002 | Carrico et al. | |
| 6,455,732 B1 * | 9/2002 | Aichinger et al. .......... | 562/598 |
| 6,472,478 B1 | 10/2002 | Funk et al. | |
| 6,503,979 B1 | 1/2003 | Funk et al. | |
| 6,504,056 B1 * | 1/2003 | Aichinger et al. .......... | 562/600 |

FOREIGN PATENT DOCUMENTS

EP   0 349 240 A2   1/1990

(Continued)

*Primary Examiner*—Bernard Lipman
(74) *Attorney, Agent, or Firm*—Roylance, Abrams, Berdo & Goodman, L.L.P.

(57) ABSTRACT

In order to produce inexpensively with high productivity a water-absorbent resin of which: the residual monomer content and the water-extractable content are both low, and the properties are high, and the colorability is low; there is provided a process for producing a water-absorbent resin, which is a process for producing a crosslinked water-absorbent resin by polymerizing a monomer component including acrylic acid and/or its salt in a major proportion wherein the acrylic acid is a product obtained by catalytic gas phase oxidation of propylene and/or propane, with the process being characterized by comprising the steps of: preparing the monomer component from an acrylic acid composition that includes the unneutralized acrylic acid and a methoxyphenol and has a methoxyphenol content of 10 to 160 ppm by weight (based on the unneutralized acrylic acid); and then carrying out radical and/or ultraviolet polymerization of the resultant monomer component.

47 Claims, 1 Drawing Sheet

FOREIGN PATENT DOCUMENTS

| | | |
|---|---|---|
| EP | 0 349 240 B1 | 1/1990 |
| EP | 0 450 923 A2 | 10/1991 |
| EP | 0 450 924 A2 | 10/1991 |
| EP | 0 574 260 A1 | 12/1993 |
| EP | 0 605 150 A1 | 7/1994 |
| EP | 0 605 150 B1 | 7/1994 |
| EP | 0 668 080 A2 | 8/1995 |
| EP | 0 744 964 B1 | 12/1996 |
| EP | 0 811 636 A1 | 12/1997 |
| EP | 0 812 873 A1 | 12/1997 |
| EP | 0 922 717 A1 | 6/1999 |
| EP | 0 942 014 A2 | 9/1999 |
| EP | 0 955 086 A2 | 11/1999 |
| EP | 1 108 745 A1 | 6/2001 |
| EP | 1 178 059 A2 | 2/2002 |
| JP | 53-41637 | 11/1978 |
| JP | 62-54751 | 3/1987 |
| JP | 3-31306 | 2/1991 |
| JP | 6-211934 | 8/1994 |
| JP | 7-82210 | 3/1995 |
| JP | 7-224204 | 8/1995 |
| JP | 7-242709 | 9/1995 |
| WO | WO 95/22356 | 8/1995 |
| WO | WO 99/42494 | 8/1999 |
| WO | WO 99/42496 | 8/1999 |
| WO | WO 99/43720 | 9/1999 |
| WO | WO 03/014172 | 2/2003 |
| WO | WO 03/053482 | 7/2003 |
| WO | WO 03/095510 | 11/2003 |
| WO | WO 2004/052819 | 6/2004 |
| WO | WO 2004/052949 | 6/2004 |

* cited by examiner

ACRYLIC ACID COMPOSITION AND ITS PRODUCTION PROCESS, AND PROCESS FOR PRODUCING WATER-ABSORBENT RESIN USING THIS ACRYLIC ACID COMPOSITION, AND WATER-ABSORBENT RESIN

TECHNICAL FIELD

The present invention relates to a process for producing a water-absorbent resin. Furthermore, the present invention specifically relates to: a process for producing a crosslinked water-absorbent resin by polymerizing a monomer component including acrylic acid and/or its salt in a major proportion; an acrylic acid composition suitable for producing a crosslinked water-absorbent resin; a process for producing this acrylic acid composition; and a water-absorbent resin being a product obtained by the aforementioned process for producing a water-absorbent resin. The present invention more specifically relates to: a process for producing a high quality water-absorbent resin at a fast polymerization rate; an acrylic acid composition suitable for producing a water-absorbent resin at a fast polymerization rate; a process for producing this acrylic acid composition; and a water-absorbent resin product obtained by the rapid polymerization process.

BACKGROUND ART

In recent years, water-absorbent resins having a high degree of water absorbency are developed and frequently used mainly for disposable uses, for example, as absorbent articles (e.g. disposable diapers and sanitary napkins) and further as water-retaining agents for agriculture and horticulture and for industrial sealing materials.

As to such water-absorbent resins, many monomers and hydrophilic polymers are proposed as their raw materials. Of them, acrylic water-absorbent resins as obtained from acrylic acid and/or its salt as the monomers are industrially most commonly used because of their high water absorbency (e.g. JP-A-054751/1987, JP-A-031306/1991, JP-A-211934/1994, U.S. Pat. Nos. 4,654,039, 5,338,810, 5,574,121, 5,562,646, EP 0574260, EP 0942014, U.S. Pat. Nos. 5,837,789, and 5,447,727).

Because water-absorbent resins are generally used for disposable uses (such as disposable diapers), it is essential that they are inexpensive. Therefore, the enhancement of their productivity is in high demand.

In addition, there is a natural high demand for the absorbent articles to avoid problems with respect to the safety and coloring of the absorbent articles. Specifically, the water-absorbent resin contains the unreacted residue of acrylic acid. Although the content of the unreacted acrylic acid is several hundred to about 1,000 ppm by weight (mass), a decrease in the content of the unreacted acrylic acid is demanded. In addition, the water-absorbent resin is combined with white pulp in the absorbent articles. Therefore there is a high demand for the water-absorbent resin also to be white so as not to give any foreign-substance feeling or appearance caused by coloring.

In addition, the water-absorbent resin is water-swellable and water-insoluble. However, in the water-absorbent resin, there is also contained an uncrosslinked water-soluble polymer (water-extractable component) in the range of several wt % to several tens of wt %. This water-extractable component has a bad influence upon the water absorption properties of the water-absorbent resin. Therefore, the decrease of the content of this water-extractable component is also demanded. Moreover, the absorbent articles containing the water-absorbent resin is required to possess acceptable water absorption properties under load (e.g. water absorption capacity under a load and liquid permeation quantity under a load).

DISCLOSURE OF THE INVENTION

Object of the Invention

Thus, an object of the present invention is to produce inexpensively with high productivity a water-absorbent resin of which the residual monomer content and the water-extractable content are both low, and the properties are high, and the colorability is low.

SUMMARY OF THE INVENTION

As a result of diligent study to solve the above problems, the present inventors have completed the present invention by discovering that all the above problems can be solved by an easy process in which the polymerization for producing a water-absorbent resin is carried out in the presence of a methoxyphenol and where the quantity of the methoxyphenol in the reaction mixture is controlled within a specific range.

In particular, the present invention provides a process for producing a water-absorbent resin, where the process produces a crosslinked water-absorbent resin by polymerizing a monomer component including acrylic acid and/or its salt in a major proportion wherein the acrylic acid is a product obtained by catalytic gas phase oxidation of propylene and/or propane. The process is characterized by comprising the steps of: preparing the monomer component from an acrylic acid composition that includes the unneutralized acrylic acid and a methoxyphenol and has a methoxyphenol content of 10 to 160 ppm by weight (based on the weight of the unneutralized acrylic acid); and then carrying out radical and/or ultraviolet polymerization of the resultant monomer component.

In addition, the present invention further provides another process for producing a water-absorbent resin, where the process produces a crosslinked water-absorbent resin by polymerizing a monomer component including acrylic acid and/or its salt in a major proportion wherein the acrylic acid is a product obtained by catalytic gas phase oxidation of propylene and/or propane, and where the process is characterized by comprising the steps of: preparing the monomer component from an acrylic acid composition that includes the unneutralized acrylic acid; and then carrying out radical and/or ultraviolet polymerization of the resultant monomer component in the presence of a methoxyphenol in an amount of 10 to 160 ppm by weight relative to the weight of the acrylic acid and/or its salt (based on the weight in terms of the unneutralized acrylic acid) in the monomer component.

In addition, the present invention further provides another process for producing a water-absorbent resin, where the process produces a crosslinked water-absorbent resin by polymerizing a monomer component including acrylic acid and/or its salt in a major proportion wherein the acrylic acid is a product obtained by catalytic gas phase oxidation of propylene and/or propane, and where the process is characterized by comprising the steps of: treating an acrylic acid composition and/or its neutralized product with an adsorbing agent wherein the acrylic acid composition includes the unneutralized acrylic and a methoxyphenol; and then preparing the monomer component from the resultant product; and then carrying out radical and/or ultraviolet polymerization of the resultant monomer component.

In addition, the present invention further provides a water-absorbent resin, where the water-absorbent resin is a product obtained by any one of the above production processes according to the present invention, with the water-absorbent resin displaying an absorption capacity of not less than 20 g/g under a load and/or a saline flow conductivity of not less than $20 \times 10^{-7}$ ($cm^3 \cdot s \cdot g^{-1}$).

In addition, the present invention further provides a sanitary material, comprising the above water-absorbent resin produced according to the process of the present invention.

Moreover, the present invention further provides an acrylic acid composition, comprising unneutralized acrylic acid and being used in producing a crosslinked water-absorbent resin by polymerizing a monomer component including acrylic acid and/or its salt in a major proportion wherein the acrylic acid is a product obtained by catalytic gas phase oxidation of propylene and/or propane, with the acrylic acid composition being characterized by having a protoanemonin and/or furfural content of not more than 20 ppm by weight (relative to the unneutralized acrylic acid) and a methoxyphenol content of 10 to 160 ppm by weight relative to the unneutralized acrylic acid.

Moreover, the present invention further provides a process for producing an acrylic acid composition where the acid composition comprises unneutralized acrylic acid and methoxyphenol and being used in producing a crosslinked water-absorbent resin by polymerizing a monomer component including the acrylic acid and/or its salt in a major proportion wherein the acrylic acid is a product obtained by catalytic gas phase oxidation of propylene and/or propane, with the process being characterized by comprising the step of carrying out treatment of a methoxyphenol-containing acrylic acid by distillation and/or crystallization to adjust its methoxyphenol content into the range of 10 to 160 ppm by weight relative to the unneutralized acrylic acid to produce the acrylic acid composition.

DETAILED DESCRIPTION OF THE INVENTION

Figure 1:
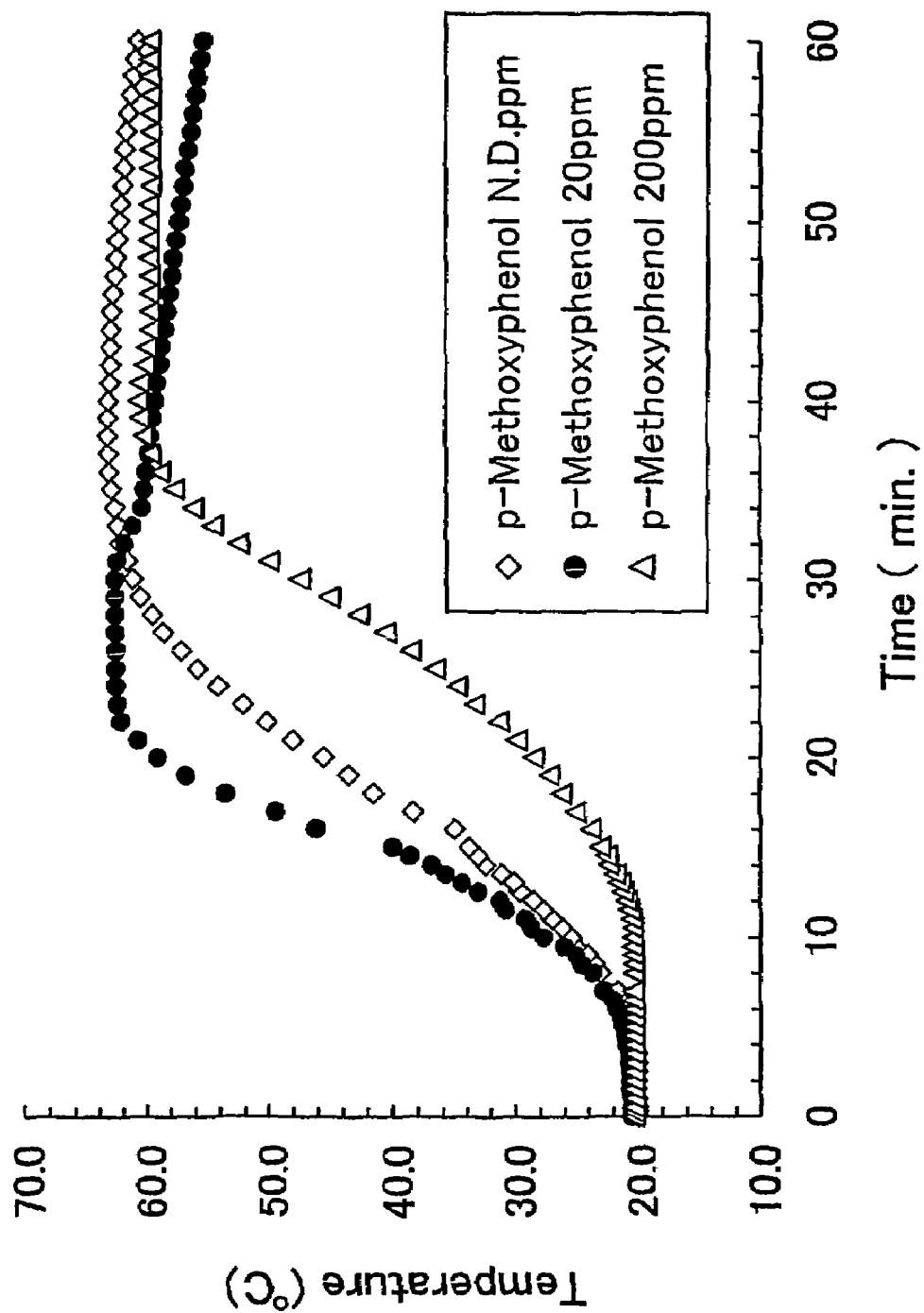
FIG. 1 is a graph which shows variations in polymerization with the passage of time in Example 1 and Comparative Examples 1 and 2.

Hereinafter, the present invention is described in more detail.

(1) Crosslinked water-absorbent resin being a product obtained by polymerizing a monomer component including acrylic acid and/or its salt in a major proportion:

The "crosslinked water-absorbent resin" in the present invention refers to a resin having water-swellability and water-insolubility as a result of introducing a crosslinked structure into the polymer, wherein the "water-swellability" means the ability to absorb at least 2 times, favorably 5 to 200 times, more favorably 20 to 100 times, as large a quantity of physiological saline solution as the mass (weight) of the resin without load, and wherein the "water-insolubility" means substantial water-insolubility such that the water-extractable content in the resin is essentially not more than 50 wt %, favorably not more than 25 wt %, more favorably not more than 15 wt %, still more favorably not more than 10 wt %. Incidentally, the methods for measuring these properties are specified in the below-mentioned description of examples of some preferred embodiments of the present invention.

In addition, the "monomer component including acrylic acid and/or its salt in a major proportion wherein the acrylic acid is a product obtained by catalytic gas phase oxidation of propylene and/or propane" (hereinafter this acrylic acid may be referred to simply as acrylic acid), as referred to in the present invention, refers to the monomer component including the acrylic acid and/or its salt in a proportion of essentially not less than 30 mol %, favorably not less than 50 mol %, more favorably not less than 70 mol %, still more favorably not less than 90 mol %, particularly favorably substantially 100 mol %, in terms of total mol % of the acrylic acid and/or its salt relative to the total monomers (exclusive of crosslinking agents) as used for the polymerization.

As to the acrylate salt used in the present invention, those which are used favorably from the viewpoint of the properties are as follows: monovalent salts of acrylic acid including alkaline metal salts, ammonium salts, and amine salts, more favorably alkaline metal acrylates, still more favorably acrylate salts selected from among sodium salt, lithium salt, and potassium salt.

The water-absorbent resin, as obtained in the present invention, is such that 20 to 99 mol %, favorably 50 to 95 mol %, more favorably 60 to 90 mol %, in terms of neutralization ratio, of the acid groups of the polymer are neutralized. This neutralization may be carried out either to the monomer component before polymerization, or to the polymer during and/or after polymerization. Furthermore, the process steps of neutralizing the monomer component and neutralizing the polymer may be combined with each other. However, it is favorable to subject acrylic acid as a monomer component to the below-mentioned alkali treatment. The preferred low discoloration, low coloring and the low residual monomer content of the water-absorbent resin of the present invention are attained by maintaining the neutralization ratio as low as possible, more favorably not higher than 75 mol %, still more favorably not higher than 70 mol %, particularly favorably not higher than 65 mol %. The lower limit of the neutralization is controlled within the aforementioned range.

Accordingly, a particularly favorable mode of the neutralization is that the neutralization ratio of the monomer component is not higher than 75 mol %.

(2) Acrylic acid composition (which may be referred to simply as acrylic acid):

Examples of known industrial processes for producing acrylic acid include a process of catalytic gas phase oxidation of propylene and/or propane, an ethylene cyanohydrin process, a high pressure Reppe process, an improved Reppe process, a ketene process, and an acrylonitrile hydrolysis process. Of them, the process of catalytic gas phase oxidation of propylene and/or propane is most commonly employed. Then, in the present invention, acrylic acid as obtained by such a catalytic gas phase oxidation process is favorably used. This acrylic acid, as obtained by the catalytic gas phase oxidation process, contains the below-mentioned impurities and usually further contains p-methoxyphenol in an amount of about 200 ppm by weight.

In the present invention, the monomer component is prepared from an acrylic acid composition. The "acrylic acid composition" as referred to in the present invention is either acrylic acid containing trace amounts of components such as a polymerization inhibitor, water, and acrylic acid dimer, or an aqueous solution of such acrylic acid, wherein the acrylic acid content is favorably not less than 75 wt %, more favorably not less than 80 wt %, still more favorably not less than 90 wt %, particularly favorably not less than 98 wt %, and wherein the acrylic acid is substantially unneutralized acrylic acid (which may hereinafter be referred to as unneutralized acrylic acid). The acrylic acid composition, referred to as such in the present invention, includes the unneutralized acrylic acid as an essential component. Incidentally, some prior documents refer to the acrylic acid composition not as such, but simply as acrylic acid or aqueous acrylic acid solution. The acrylic acid composition in the present invention also may be referred to simply as acrylic acid.

The acrylic acid composition in one of the processes according to the present invention for producing a water-absorbent resin is an acrylic acid composition containing a methoxyphenol as an essential component. Specific examples of the aforementioned methoxyphenol include o-, m-, p-methoxyphenol and methoxyphenol which have at least one substituent such as methyl, t-butyl, or hydroxyl. In one embodiment, p-methoxyphenol is particularly preferred in the process of the present invention. Hereinafter, unless otherwise noted, explanation is given with the p-methoxyphenol used as the methoxyphenol, but not to the effect that the following explanation should be interpreted as limiting the methoxyphenol to the p-methoxyphenol (incidentally, the p-methoxyphenol was used in the below-mentioned examples of some preferred embodiments of the present invention).

In one of the processes according to the present invention for producing a water-absorbent resin, the acrylic acid composition contains p-methoxyphenol (also known as hydroquinone monomethyl ether) as an essential component, and this content is essentially in the range of 10 to 160 ppm by weight relative to the weight of the unneutralized acrylic acid (solid content of the acrylic acid). Incidentally, the unneutralized acrylic acid, referred to as the base of the above content, for example, means unneutralized acrylic acid containing trace amounts of components (such as a polymerization inhibitor, water, and acrylic acid dimer) as impurities.

In the case where the p-methoxyphenol content is more than 160 ppm by weight, not only is the polymerization rate so slow as to result in low productivity, but there also occurs a problem that the resultant water-absorbent resin becomes colored and exhibits yellowing (becomes tinged with yellow/turns yellow). In addition, it has been discovered by the present inventors that: in the case where the p-methoxyphenol content is less than 10 ppm by weight, particularly less than 5 ppm by weight, in other words, in the case where the p-methoxyphenol which is a polymerization inhibitor has been removed such as by distillation, not only is there a danger that the polymerization will take place before intentionally being initiated, but also, surprisingly, the polymerization rate rather becomes slow. In other words, it has been discovered by the present inventors that a specific quantity of p-methoxyphenol, which is a polymerization inhibitor, coexisting with the monomer in the reaction mixture promotes the polymerization and the production of the water-absorbent resin without yellowing or discoloration.

The lower limit of the p-methoxyphenol content is favorably not less than 20 ppm by weight, more favorably not less than 30 ppm by weight, still more favorably not less than 40 ppm by weight, particularly favorably not less than 50 ppm by weight. In addition, the upper limit of the p-methoxyphenol content is favorably not more than 140 ppm by weight, more favorably not more than 120 ppm by weight, still more favorably not more than 100 ppm by weight, particularly favorably not more than 90 ppm by weight. Specifically for example, the p-methoxyphenol content is in the range of 20 to 140 ppm by weight, favorably 30 to 120 ppm by weight, more favorably 40 to 100 ppm by weight, still more favorably 50 to 90 ppm by weight.

Furthermore, in another process according to the present invention for producing a water-absorbent resin, the polymerization of the monomer component is carried out in the presence of the methoxyphenol of an amount of 10 to 160 ppm by weight relative to the weight of the acrylic acid and/or its salt (based on the weight in terms of the unneutralized acrylic acid) in the monomer component.

The problems occurring in the case where the above methoxyphenol content is more than 160 ppm by weight or less than 10 ppm by weight are the same as the aforementioned, and the favorable values of the upper and lower limits of the above methoxyphenol content are also the same as the aforementioned.

Incidentally, because there is a difference in weight between acrylic acid and its salt, the "methoxyphenol of an amount of 10 to 160 ppm by weight relative to the acrylic acid and/or its salt" in the present invention is a methoxyphenol content (weight of the methoxyphenol) relative to a weight resulting from the conversion of the total weight of the acrylic acid and/or its salt into the unneutralized acrylic acid. Specifically, the weight of neutralized sodium acrylate (molecular weight: 94) is converted into that of acrylic acid (molecular weight: 72) to specify the p-methoxyphenol content (weight ratio of the p-methoxyphenol) based on a weight resulting from this conversion into that of acrylic acid (94 is converted into 72).

Incidentally, in the acrylic acid composition according to the present invention, other polymerization inhibitors can be used besides the p-methoxyphenol. For example, hydroquinone, copper salts, and Methylene Blue are effective polymerization inhibitors.

In the present invention, examples of processes for obtaining the acrylic acid composition having a p-methoxyphenol content of 10 to 160 ppm by weight (relative to the unneutralized acrylic acid) include the following (A) to (D), but there is no limitation thereto.

(A) A process including the step of distilling commercially available acrylic acid containing p-methoxyphenol as a polymerization inhibitor in an amount of 200 ppm by weight or an aqueous solution of this acrylic acid, thereby adjusting the p-methoxyphenol (boiling point: 113–115° C./5 mmHg) content of the acrylic acid (boiling point: 139° C.), thus obtaining a distilled acrylic acid having the p-methoxyphenol content as defined in the present invention.

(B) A process including the step of adding p-methoxyphenol as a polymerization inhibitor to acrylic acid or its aqueous solution in the quantity as defined in the present invention wherein the source of acrylic acid initially contains no p-methoxyphenol or substantially no p-methoxyphenol.

(C) A process including the step of adjusting the p-methoxyphenol (as polymerization inhibitor) content to that defined in the present invention in a process for producing acrylic acid.

(D) A process including the step of blending acrylic acids having different p-methoxyphenol contents, thereby adjusting the p-methoxyphenol content to that defined in the present invention.

Incidentally, specific examples of processes for obtaining the acrylic acid composition having a p-methoxyphenol content of 10 to 160 ppm by weight (relative to the weight of the unneutralized acrylic acid) from the commercially available acrylic acid having a p-methoxyphenol content of 200 ppm by weight in (A) above include processes involving distillation, crystallization, or adsorption by ion-exchange resins. Hereinafter, examples of the process involving the distillation or crystallization are illustrated.

① A process including the steps of: distilling the commercially available acrylic acid with a distillation column having a condenser, a distillate-extracting tube, and a reflux-supplying tube at a top portion of the column and further having a boiler and a raw-material-liquid-supplying tube at a lower portion of the column and still further having a stabilizing-agent-supplying tube at an upper portion of the condenser; and, while adding p-methoxyphenol from the stabilizing-agent-supplying tube, obtaining the acrylic acid composition having a p-methoxyphenol content of 10 to 160 ppm by weight.

② A process including the step of introducing the commercially available acrylic acid into a crystallizer, thereby obtaining the acrylic acid composition having a p-methoxyphenol content of 10 to 160 ppm by weight.

How to add the p-methoxyphenol during the distillation in the former process ① above is not especially limited. The p-methoxyphenol may be added either directly in the form of a powder, or in the form of a solution in the acrylic acid. Favorably for obtaining the acrylic acid composition containing the p-methoxyphenol in a stable concentration, the p-methoxyphenol is added from the upper portion of the condenser in the form of the solution in the acrylic acid. Suitable devices that can be used in the latter process ② above are disclosed in JP-B-041637/1978.

The above processes ① and ② are favorably used in the present invention. That is to say, the present invention further provides a process for producing an acrylic acid composition, where the process for producing an acrylic acid composition comprises unneutralized acrylic acid. The acrylic acid composition is used in producing a crosslinked water-absorbent resin by polymerizing a monomer component including acrylic acid and/or its salt in a major proportion wherein the acrylic acid is a product obtained by catalytic gas phase oxidation of propylene and/or propane, with the process being characterized by comprising the step of treating methoxyphenol-containing acrylic acid by distillation and/or crystallization to adjust its methoxyphenol content into the range of 10 to 160 ppm by weight relative to the weight of unneutralized acrylic acid.

Incidentally, some commercially available acrylic acids have a p-methoxyphenol content of about 200 ppm by weight. In addition, there are also known techniques involving removal of impurities such as polymerization inhibitors and acrylic acid dimer (which are impurities) by purification of acrylic acid in preparation for polymerization in producing the water-absorbent resin (JP-A-211934/1994, JP-A-031306/1991, EP 0942014, EP 0574260). However, in the case where acrylic acid is distilled in preparation for its polymerization, the p-methoxyphenol content of acrylic acid is substantially ND (Non-Detectable/detection limit 1 ppm by weight/quantified with UV) after the distillation due to the difference between boiling points of acrylic acid and p-methoxyphenol. Accordingly, even if techniques as conventionally carried out for purifying acrylic acid are applied to the commercially available acrylic acids having a p-methoxyphenol content of about 200 ppm by weight, it is impossible or extremely difficult to adjust the p-methoxyphenol content into the specific range of 10 to 160 ppm by weight. Such an adjustment needs to intentionally carry out processes such as the above processes (A) to (D).

Thus, there has never been a technical idea of: using the p-methoxyphenol as a polymerization inhibitor in conventional processes for producing acrylic acid; and using the p-methoxyphenol as a polymerization inhibitor after adjusting the quantity of the p-methoxyphenol to a range of 10 to 160 ppm by weight relative to the weight of the acrylic acid and/or its salt In addition, it has been discovered by the present inventors that: in the case where the polymerization is carried out using the commercially available acrylic acid having a p-methoxyphenol content of 200 ppm by weight, most of the p-methoxyphenol is consumed during the polymerization, although a portion of the p-methoxyphenol may remain (in the range of several ppm by weight to 100 and several ppm by weight) in the resultant water-absorbent resin.

In cases, such as cases of conventional water-absorbent resins, where fine particles having particle diameters of not larger than 150 μm are present in a quantity of not less than 10 wt % even it, as mentioned above, the methoxyphenol remains in the range of several ppm by weight to several hundreds ppm by weight, this quantity of the methoxyphenol remaining in the water-absorbent resin does not have a influence on coloring and does not cause yellowing of the water-absorbent resin. However, it has been discovered by the present inventors that, in the case of a water-absorbent resin in which the quantity of fine particles having particle diameters of not larger than 150 μm is less than 10 wt %, favorably not more than 5 wt %, the quantity of the methoxyphenol remaining in this water-absorbent resin has a great influence on coloring (such as yellowing) of this water-absorbent resin. Furthermore, the present inventors have discovered that, if the quantity of the methoxyphenol is adjusted to the specific quantity of 10 to 160 ppm by weight relative to the weight of the unneutralized acrylic acid, then excellent results are obtained with regard to the stability of the monomer component during its preservation, the polymerization rate of the polymerization reaction, and the quality of water-absorbent resin after polymerization.

In addition, it is favorable that the acrylic acid composition according to the present invention has a protoanemonin and/or furfural content of not more than 20 ppm by weight As the protoanemonin and/or furfural content increases, not only does the polymerization time (time passing until the polymerization temperature reaches its peak) become longer to increase the residual monomer content, but also the water-extractable content increases much more than the small increase in the water absorption capacity, resulting in relative deterioration of properties. From the viewpoint of the enhancements of the properties and performances of the resultant water-absorbent resin, the protoanemonin and/or furfural content of the acrylic acid is more favorably not more than 10 ppm by weight, still more favorably in the range of 0.01 to 5 ppm by weight, yet still more favorably 0.05 to 2 ppm by weight, particularly favorably 0.1 to 1 ppm by weight.

That is to say, in the present invention, it is favorable that the acrylic acid composition has a protoanemonin and/or furfural content of not more than 20 ppm by weight (relative to the monomers).

In addition, it is favorable that the acrylic acid composition according to the present invention has a protoanemonin and/or furfural content of not more than 20 ppm by weight (relative to the unneutralized acrylic acid). In proportion as the protoanemonin and/or furfural content increases, not only does the polymerization time (time passing until the polymerization temperature reaches its peak) become longer to increase the residual monomer content, but also the water-extractable content increases much more than the small increase of the water absorption capacity, resulting in relative deterioration of properties. From the viewpoint of the enhancements of the properties and performances of the resultant water-absorbent resin, the protoanemonin and/or furfural content of the acrylic acid composition is more favorably not more than 10 ppm by weight, still more favorably in the range of 0.01 to 5 ppm by weight, yet still more favorably 0.05 to 2 ppm by weight, particularly favorably 0.1 to 1 ppm by weight, relative to the unneutralized acrylic acid.

The above acrylic acid composition having a protoanemonin and/or furfural content of not more than 20 ppm by weight can be obtained by processes such as controlling the purification method in the production process or further distilling or purifying a purified acrylic acid, and the quantification of this composition can be carried out by processes such as gas chromatography.

From the above, the present invention further provides an acrylic acid composition, comprising unneutralized acrylic acid and being used in producing a crosslinked water-absorbent resin by polymerizing a monomer component including acrylic acid and/or its salt in a major proportion wherein the acrylic acid is a product obtained by catalytic gas phase oxidation of propylene and/or propane, with the acrylic acid composition being characterized by having a protoanemonin and/or furfural content of not more than 20 ppm by weight (relative to the unneutralized acrylic acid) and a methoxyphenol content of 10 to 160 ppm by weight relative to the unneutralized acrylic acid.

(3) Step of preparing the monomer component from the acrylic acid composition:

The process for producing a water-absorbent resin, according to the present invention, includes the step of preparing the monomer component from the aforementioned acrylic acid composition, when it is favorable to subject the aforementioned acrylic acid composition to alkali treatment.

The alkali treatment, as referred to in the present invention, means a treatment in which the acrylic acid composition to be treated is added to a large amount of alkali or combined with an alkali all at once, and in which acrylic acid that contains the aforementioned impurities, that is, the acrylic acid composition, is treated at not lower than a certain temperature under alkaline conditions, particularly under strong alkaline conditions. The polymerization of acrylic acid is greatly promoted by such an alkali treatment.

Examples of basic substances as used for the alkali treatment include (hydrogen)carbonate salts, alkaline-metal hydroxides, ammonia, and organic amines. However, to further enhance the polymerizability of the acrylic acid monomer component and for obtaining a water-absorbent resin having still higher properties, the strong-alkali treatment preferably treats the acrylic acid composition with the alkaline-metal hydroxides such as sodium hydroxide, potassium hydroxide, and lithium hydroxide is where sodium hydroxide is particularly preferred. These alkali treatments are preferably in the presence of an excess of alkali so that the neutralization ratio of acrylic acid in the acrylic acid composition is substantially 100 mol %. The amount of alkali can be more than is necessary to neutralize 100 mol% of the acrylic acid. Specific examples thereof include: a process in which the acrylic acid composition is gradually added to a certain amount of alkaline substance to get a strong alkaline region; and a process in which the alkali treatment is carried out simultaneously with the neutralization by line-mixing the acrylic acid composition and a strong alkali together. In addition, or otherwise, in a process in which an alkali is gradually added to a large excess of acrylic acid composition, the amount of acrylic acid in the acrylic acid composition is always greater than the amount of alkali, so that the neutralization amount is less than 100%, and there is a possibility that the polymerizability may tend to be insufficient, and that weak bases (e.g. (hydrogen)carbonate salts) which are often used in general for neutralization of acrylic acid may also be insufficient to enhance the polymerizability following the alkali treatment.

In the alkali treatment, particularly, strong-alkali treatment, the acrylic acid composition is treated in such a manner to form an aqueous solution or dispersion having a concentration of favorably 10 to 80 wt %, more favorably 20 to 60 wt %, still more favorably 30 to 50 wt %. The time of such an alkali treatment, particularly the treatment time in the case of carrying out the alkali treatment in the presence of an excess of the alkali, is appropriately determined in the range of favorably 1 second to 48 hours, more favorably 1 minute to 36 hours, still more favorably 5 minutes to 24 hours, particularly favorably 30 minutes to 24 hours. In addition, in the case where the alkali treatment is carried out in a high alkaline region, favorably in tie presence of an excess of the alkali, more favorably with an excessive amount of the alkali reaching not less than 105 mol % of that necessary to neutralize 100 mol % of the acrylic acid, this alkali treatment may be carried out jointly with an alkali treatment in which acrylic acid is stored or aged for a long time, favorably not shorter than 10 hours, more favorably not shorter than 20 hours, still more favorably not shorter than 40 hours.

The temperature of the acrylic acid composition or its aqueous solution in the alkali treatment is kept favorably not lower than 20° C., more favorably not lower than 30° C., still more favorably not lower than 40° C., particularly favorably not lower than 50° C. As to the alkali treatment, in cases where the temperature is low and where no strong alkali is used and further where the neutralization has not yet been completed, the polymerizability is so low that inferior results are also obtained with regard to the properties even if a superpurified acrylic acid is used. Furthermore, the alkali treatment is carried out in the presence of oxygen for stability, preferably, in a state where the aqueous acrylic acid (or salt) solution contains oxygen in the range of 0.5 to 20 ppm, more favorably 1 to 15 ppm, still more favorably 1.5 to 10 ppm. In the case where the oxygen content is low, there are problems of the stability of the monomer in the alkali treatment. The alkali treatment is favorably carried out under an oxygen or air atmosphere, more favorably, while oxygen or air is blown in and/or drawn in. Incidentally, the oxygen content is measurable with a dissolved oxygen meter.

Furthermore, after the alkali treatment, it is favorable that the resultant acrylic acid and/or its salt, that is, the resultant acrylic acid composition and/or its neutralized product, is brought into contact with an adsorbing agent such as active carbon and, also favorably, further filtered. The adsorbing agent is used favorably in the ratio of not less than 0.001 part by weight, more favorably not less than 0.1 part by weight, to 100 parts by weight (in terms of solid content) of the acrylic acid and/or its salt, and the temperature during the treatment is favorably in the range of 0 to 60° C., more favorably 10 to 40° C. Although there is no specific upper limit of the quantity of the adsorbing agent such as active carbon, yet, from the viewpoint of the economical advantage, the adsorbing agent is used favorably in the ratio of not more than 100 parts by weight, more favorably not more than 10 parts by weight, to 100 parts by weight (in terms of solid content) of the acrylic acid and/or its salt. The contact of the acrylic acid and/or its salt with these adsorbing agents is carried out continuously or batchwise under conditions where the acrylic acid and/or its salt is in the form of an aqueous solution. These adsorption treatments more satisfactorily achieve the aforementioned object of the present invention, further reduce the residual monomer content and the water-extractable content, enhance the gel stability (urine resistance, light resistance) as well, and also produce a water-absorbent resin having still higher properties and still lower colorability with low yellowing.

In addition, in the present invention, the turbidity (according to JIS K-0101) of the acrylic acid composition and/or its neutralized product, as obtained by the above treatment, is favorably not more than 0.5. In the case where the turbidity is more than 0.5 after the treatment with such as active carbon, the gel durability (light resistance, urine resistance) may be deteriorated. Therefore, it is favorable to adjust the turbidity to not more than 0.5 by appropriately controlling the filter and/or number of times of the filtration.

That is to say, the present invention further provides another process for producing a water-absorbent resin, which is a process for producing a crosslinked water-absorbent resin by polymerizing a monomer component including acrylic acid and/or its salt in a major proportion wherein the acrylic acid is a product obtained by catalytic gas phase oxidation of propylene and/or propane, with the process being characterized by comprising the steps of: treating an acrylic acid composition and/or its neutralized product with an adsorbing agent wherein the acrylic acid composition includes the unneutralized acrylic acid and a methoxyphenol; and then preparing the monomer component from the resultant product; and then carrying out radical and/or ultraviolet polymerization of the resultant monomer component.

In the above production process, the methoxyphenol content of the acrylic acid composition may be about 200 ppm by weight, but is favorably in the range of 10 to 160 ppm by weight relative to the unneutralized acrylic acid.

In the above production process, the turbidity (according to JIS K-0101) of the acrylic acid composition and/or its neutralized product is favorably not more than 0.5 after the above treatment with the adsorbing agent.

As is mentioned above, the monomer component includes acrylic acid and/or its salt in a major proportion, but another monomer may be used jointly therewith. Examples of this monomer that can be jointly used include monomers as disclosed in U.S. patents such as U.S. Pat. Nos. 4,093,776, 4,286,082, 4,367,323, 4,446,261, 4,625,001, 4,683,274, 4,873,299, 4,973,632, 4,985,518, 5,124,416, 5,244,735, 5,250,640, 5,264,495, 5,145,906, and 5,380,808, and in European patents such as EP 0811636, EP 0955086, and EP 0922717. Specific examples thereof further include copolymers as obtained by copolymerizing the acrylic acid and/or its salt with, for example, water-soluble or hydrophobic unsaturated monomers such as methacrylic acid, (anhydrous) maleic acid, fumaric acid, crotonic acid, itaconic acid, vinylsulfonic acid, 2-(meth)acrylamido-2-methylpropanesulfonic acid, (meth)acryloxyalkanesulfonic acid, and their alkaline metal salts and ammonium salts, and further, N-vinyl-2-pyrrolidone, N-vinylacetamide, (meth)acrylamide, N-isopropyl(meth)acrylamide, N,N-dimethyl(meth)acrylamide, 2-hydroxyethyl (meth)acrylate, methoxypolyethylene glycol (meth)acrylate, polyethylene glycol (meth)acrylate, isobutylene, and lauryl (meth)acrylate.

The crosslinking method as used in the present invention is not especially limited, but examples thereof include: (A) a method which involves the steps of obtaining a hydrophilic polymer by the polymerization of acrylic acid and/or its salt or, if necessary, copolymerization thereof with the above water-soluble or hydrophobic unsaturated monomers, and then adding a crosslinking agent to the resultant hydrophilic polymer during and/or after the polymerization, thereby post-crosslinking the hydrophilic polymer; (B) a method which involves radical crosslinking with radical polymerization initiators; and (C) a method which involves radiation crosslinking such as by electron beams. However, a favorable one is (D) a method which involves the steps of beforehand adding a predetermined amount of an internal-crosslinking agent to acrylic acid and/or its salt or to the above water-soluble or hydrophobic unsaturated monomers as comonomers, and then carrying out polymerization simultaneously with and/or after which a crosslinking reaction is carried out. As a matter of course, the crosslinking method (D) may be employed jointly with the crosslinking methods (A) to (C).

Examples of the internal-crosslinking agent, as used in the above method (D), include N,N'-methylenebisacrylamide, (poly)ethylene glycol di(meth)acrylate, (poly)propylene glycol di(meth)acrylate, (polyoxyethylene) trimethylolpropane tri(meth)acrylate, trimethylolpropane di(meth)acrylate, polyethylene glycol di($\beta$-acryloyloxypropionate), trimethylolpropane tri($\beta$-acryloyloxypropionate), poly(meth)allyloxyalkanes, polyethylene glycol diglycidyl ether, ethylene glycol, polyethylene glycol, and glycerol. These internal-crosslinking agents may be used either alone or in combinations with each other. Incidentally, when at least one internal-crosslinking agent is used, it is favorable in consideration of, for example, the absorption properties of the resultant water-absorbent resin that a compound with at least two polymerizable unsaturated groups as an essential component is used during the polymerization.

The amount of the above internal-crosslinking agent as used is favorably in the range of 0.005 to 2 mol %, more favorably 0.01 to 1 mol %, still more favorably 0.05 to 0.2 mol %, relative to the aforementioned monomer component. In the case where the amount of the above internal-crosslinking agent is smaller than 0.005 mol % or larger than 2 mol %, there is a possibility that the desired absorption properties may not be obtained.

When the monomer component is used in the form of its aqueous solution in the case where reversed-phase suspension polymerization or aqueous solution polymerization is carried out in the polymerization step, the concentration of the monomer component in this aqueous solution (hereinafter referred to as "aqueous monomer solution") is in the range of favorably 10 to 70 wt %, more favorably 15 to 65 wt %, still more favorably 30 to 55 wt %, in view of the resulting properties, although not especially limited. In addition, when the above aqueous solution polymerization or reversed-phase suspension polymerization is carried out, a solvent other than water may be used jointly therewith if necessary, and the kind of this solvent as jointly used is not especially limited.

Incidentally, when the polymerization is carried out, components such as various foaming agents (e.g. carbonate salts, azo compounds, bubbles), hydrophilic polymers, surfactants, and chelating agents can be added for improving the properties of the water-absorbent resin. For example, to the polymerization system there may be added the following materials: various foaming agents such as carbonate salts (or hydrogencarbonate salts), carbon dioxide, nitrogen, azo compounds, and inert organic solvents in a quantity of 0 to 5 wt % (relative to solid content of monomers); hydrophilic polymers such as starch, cellulose, their derivatives, poly (vinyl alcohol), poly(acrylic acid) (or its salts), and crosslinked polymers of poly(acrylic acid) (or its salts) in a quantity of 0 to 30 wt % (relative to solid content of monomers); various surfactants; and chain transfer agents such as hypophosphorous acid (or its salts) in a quantity of 0 to 1 wt % (relative to solid content of monomers).

(4) Step of carrying out polymerization:

In the step of polymerizing the monomer component, it is favorable, from the viewpoint of the performance or the ease of controlling the polymerization, to carry out aqueous solution polymerization or reversed-phase suspension polymerization in which the above monomer component is used in the form of its aqueous solution. These polymerization methods are carried out favorably under an atmosphere of an inert gas such as nitrogen or argon. In addition, the monomer component is used for polymerization favorably after oxygen dissolved therein has sufficiently been displaced with the inert gas. The present invention is particularly favorable for the aqueous solution polymerization which is of high productivity and gives high properties but conventionally involves difficulty in controlling the polymerization. Examples of particularly favorable aqueous solution polymerization include continuous belt polymerization and continuous or batch kneader polymerization.

Incidentally, the reversed-phase suspension polymerization is a polymerization method in which the aqueous monomer solution is suspended into a hydrophobic organic solvent, and examples thereof are disclosed in U.S. patents such as U.S. Pat. Nos. 4,093,776, 4,367,323, 4,446,261, 4,683,274, and 5,244,735. The aqueous solution polymerization is a polymerization method in which the aqueous monomer solution is polymerized without using any dispersion solvent, and examples thereof are disclosed in U.S. patents such as U.S. Pat. Nos. 4,625,001, 4,873,299, 4,286,082, 4,973,632, 4,985,518, 5,124,416, 5,250,640, 5,264,495, 5,145,906, and 5,380,808, and in European patents such as EP 0811636, EP 0955086, and EP 0922717.

Furthermore, in the present invention, when the aforementioned monomer component is polymerized, the total time of from the end of the preparation of the monomer component and/or neutralization of the acrylic acid until the initiation of tie polymerization is as short as possible favorably for attaining the reduction of the residual monomer content and the low coloring or yellowing which are the goals of the present invention,. Specifically, the polymerization is initiated favorably within 24 hours, more favorably within 12 hours, still more favorably within 3 hours, particularly favorably within 1 hour, after the preparation of the monomer component and/or neutralization of the acrylic acid. Industrially, the neutralization and/or the preparation of the monomer component are carried out in large quantities in tanks. Therefore it is usual that the residence time exceeds 24 hours. However, it has been discovered by the present inventors that the longer time it is after the preparation of the monomer component and/or neutralization of the acrylic acid, the more the residual monomer content and the low coloring and low yellowing are deteriorated. Thus, to shorten the residence time, the neutralization and the preparation of the monomer component are continuously made to carry out the polymerization batchwise or continuously. Preferably, the polymerization is carried out continuously.

When the above aqueous monomer solution is polymerized, at least one of the following polymerization initiators, for example, can be used: persulfate salts such as potassium persulfate, ammonium persulfate, and sodium persulfate; and t-butyl hydroperoxide, hydrogen peroxide, 2,2'azobis(2-amidinopropane) dihydrochloride, 2-hydroxy-1-phenylpropan-1-one, and benzoin methyl ether. Furthermore, a redox initiator is also available by using the above polymerization initiator jointly with a reducing agent which promotes decomposition of the above polymerization initiator and thus combining both with each other. Examples of the above reducing agent include: sulfurous acid (or (bi)sulfite salts) such as sodium sulfite and sodium hydrogensulfite; L-ascorbic acid (or its salts);. reducible metals (or their salts) such as ferrous salts; and amines; and favorably used is a redox polymerization initiator combining the reducing agent with the persulfate salt and/or the peroxide, but there is no particular limitation thereto. The amount of the above polymerization initiator or reducing agent as used is usually in the range of favorably 0.001 to 2 mol %, more favorably 0.01 to 0.5 mol %, relative to the monomer component.

Of these polymerization initiators, favorably for attaining still lower colorability and lower yellowing of the water-absorbent resin of the present invention, the hydrogen peroxide and/or the (hydrogen)sulfite salts, more favorably the hydrogen peroxide, are used. Other polymerization initiators, particularly the persulfate salts or the azo compounds, may further be used in combination with the hydrogen peroxide and/or (hydrogen) sulfite salts. The quantity of the hydrogen peroxide and/or the (hydrogen)sulfite salts as used is favorably in the range of 0.00001 to 0.1 g/(mol of monomers), more favorably 0.0001 to 0.01 g/(mol of monomers), and further is smaller than that of the above other polymerization initiators as used jointly therewith. Incidentally, the azo compounds display a good effect on the low coloring and low yellowing, but excessive use of the persulfate salts brings about property deterioration and/or coloring and yellowing. Therefore the persulfate salts are jointly used favorably in the aforementioned range.

It has been discovered by the present inventors that, in the present invention, hydrogen peroxide as an oxidizing agent displays unexpectedly a good effect on decreasing the coloring and yellowing when used in combination with the methoxyphenol.

That is to say, as to the polymerization, the process according to the present invention exhibits great effects on aqueous solution polymerization (radical and/or ultraviolet polymerization) involving the use of radical polymerization initiators and/or ultraviolet polymerization initiators, and the polymerization initiation temperature as favorably adopted is not lower than 20° C., more favorably not lower than 30° C., still more favorably not lower than 40° C., particularly favorably not lower than 50° C.

In addition, for the promotion of the polymerization, it is favorable that the monomer component to be polymerized further contains a trace amount of a transition metal. In other words, in the present invention, it is favorable that the aforementioned step of carrying out the radical and/or ultraviolet polymerization is carried out in the presence of a transition metal ion. The aforementioned transition metal is present usually in the form of the transition metal ion. Although the aforementioned transition metal is not especially limited, iron is particularly favorable. As to the content of the transition metal as used, the transition metal ion is present favorably in the range of 0 to 5 ppm by weight (the weight of the transition metal ion is calculated in terms of transition metal), more favorably 0.1 to 2 ppm by weight, still more favorably 0.2 to 1 ppm by weight, in the monomer component. In the case where the quantity of the transition metal is excessive, the residual monomer content and/or water-extractable content tends to increase. On the other hand, in the case where the quantity of the transition metal is too small, the polymerization rate tends to be low.

In addition, the polymerization reaction may be carried out either by irradiating the reaction system with active energy rays, such as radiations, electron beams, and ultraviolet rays, instead of using the above polymerization initiator, or by the joint use of these active energy rays with the above polymerization initiator. Incidentally, the reaction temperature and time in the above polymerization reaction is not particularly limited and may appropriately be set according to factors such as the respective kinds of the hydrophilic monomer and polymerization initiator and the reaction temperature. However, the polymerization is usually carried out at not higher than the boiling point favorably within 3 hours, more favorably within 1 hour, still more favorably within 0.5 hour, and at a peak temperature of favorably not higher than 150° C., more favorably in the range of 90 to 120° C. In addition, it is also favorable that water and/or acrylic acid as vaporized during the polymerization is, if necessary, collected and then recycled to the process for producing the water-absorbent resin.

In addition, the present invention is fit for production, particularly, continuous production, on a large scale of not smaller than a certain quantity per line. There is a possibility that the effects of the present invention may not sufficiently be displayed in production on a laboratory level or in production at pilot or small-scale plants. However, as to production on a large scale, particularly, of favorably not smaller than 300 Kg/hour, more favorably not smaller than 500 Kg/hour, still more favorably not smaller than 700 Kg/hour, in terms of production per line, it has been discovered by the present inventors that, also from the viewpoint of such as monomer stability and polymerization rate, unless the present invention is applied thereto, the desired water-absorbent resin having sufficient properties is not obtained.

(5) Favorable steps after polymerization (drying, pulverizing, surface-crosslinking after polymerization):

The crosslinked hydrogel polymer resulting from the polymerization step is then disintegrated into fine pieces with such as a meat chopper or a gel pulverizer of Japanese Patent Application No. 2001-232734 (EP 1178059A), if necessary, and then favorably dried, and, if necessary, then pulverized or classified and further then granulated. The water-absorbent resin according to the present invention has high properties, and these properties are improved by processing the resin by these steps.

In addition, the time from the end of the polymerization, via a gel-pulverizing step if necessary, until the start of the drying is also as short as possible favorably for attaining the reduction of the residual monomer content and the low coloring and low yellowing which are also desired by the present invention. Specifically, the crosslinked hydrogel polymer starts to be dried (is placed into a dryer) favorably within 1 hour, more favorably within 0.5 hour, still more favorably within 0.1 hour, after the polymerization is completed. In addition, to attain the reduction of the residual monomer content and the low colorability, the temperature of the crosslinked hydrogel polymer from the end of the polymerization until the start of the drying preferably is controlled in the range of 50 to 80° C., more favorably 60 to 70° C.

On industrial occasions, the polymerization is carried out in large quantities, therefore it is also usual that the residence time, after the polymerization, exceeds 3 hours. However, it has been discovered by the present inventors that as the time increases before the start of the drying and/or as the temperature deviates from the above range, the residual monomer content increases or the coloring or yellowing increases. Thus, favorably, continuous polymerization and continuous drying are carried out to shorten the residence time.

In the present invention, the drying is an operation to remove water, in which the solid content of the resin as determined from its weight loss by the drying (by heating 1 g of powder at 180° C. for 3 hours) is adjusted to favorably not less than 80 wt %, more favorably into the range of 85 to 99 wt %, still more favorably 90 to 98 wt %, particularly favorably 92 to 97 wt %. In addition, the drying temperature may be set, for example, favorably in the range of 100 to 300° C., more favorably 150 to 250° C., although not especially limited. Examples of usable drying methods include various methods such as: heat-drying; hot-wind or hot gas drying; vacuum drying; infrared drying; microwave drying; drum drier drying; dehydration by azeotropy with hydrophobic organic solvents; and high-moisture drying by high-temperature steaming. Although the drying method is therefore not especially limited, the preferred method is the hot-wind drying with a gas having a dew point of 40 to 100° C., more favorably 50 to 90° C. by directing or blowing a flow of hot gas over or through a bed of the water-absorbent resin.

The shape of the water-absorbent resin as obtained in the present invention is not especially limited, but examples thereof include: powdery shapes such as irregular pulverized shapes and spherical shapes; and gel shapes, sheet shapes, bar shapes, fibrous shapes, and filmy shapes. In addition, the resin may be combined with or supported on materials such as fibrous materials.

In the case where the water-absorbent resin is powdery, the weight-average particle diameter (D50) thereof is usually favorably in the range of 10 to 2,000 μm and, more favorably in view of the properties, in the range of 100 to 1,000 μm, still more favorably 200 to 600 μm, particularly favorably 300 to 500 μm. The quantity of particles having particle diameters in the range of 850 to 150 μm is favorably not less than 90 wt %, more favorably not less than 95 wt %. In addition, favorably, particles having particle diameters in the range of 300 to 600 μm are main components of the water-absorbent resin.

Incidentally, the weight-average particle diameter (D50) is, as disclosed in such as U.S. Pat No. 5,061,259, defined as follows. That is to say, in the case where 50 wt % of the entire particles are classified with a standard sieve having a certain mesh opening size, this mesh opening size of the standard sieve is taken as the weight-average particles diameter (D50). For example, in the case where 50 wt % of the entire particles are classified with a standard sieve having a mesh opening size of 300 μm, the weight-average particle diameter (D50) is 300 μm. Incidentally, the detail of the method for measuring the weight-average particles diameter (D50) is specified as the measurement method (9) in the below-mentioned description of examples of some preferred embodiments of the present invention.

In cases, such as cases of conventional water-absorbent resins, where fine particles having particle diameters of not larger than 150 μm are present in a quantity of not less than 10 wt % even if, as mentioned above, the methoxyphenol remains in the range of several wt % to several hundreds of wt %, this quantity of the methoxyphenol remaining in the water-absorbent resin does not have a influence on coloring (such as yellowing) of the water-absorbent resin. However, it has been discovered by the present inventors that, in the case of a water-absorbent resin in which the quantity of fine particles having particle diameters of not larger than 150 μm is less than 10 wt %, favorably not more than 5 wt %, the quantity of the methoxyphenol remaining in this water-absorbent resin has a great influence on coloring (such as yellowing) of this water-absorbent resin. Furthermore, the present inventors have discovered that, if the quantity of the methoxyphenol is adjusted to the specific quantity of 10 to 160 ppm by weight relative to the unneutralized acrylic acid, then excellent results are provided with regard to the stability of the monomer component during its preservation, the promotion of the polymerization reaction, and the quality of water-absorbent resin after polymerization.

Next, a further explanation is made about the surface-crosslinking in the present invention.

The "surface-crosslinking" of the water-absorbent resin means forming a uniformly crosslinked structure inside the polymer and further forming a portion having high crosslinking density in surface layers (neighborhoods of surfaces: neighborhoods usually within several tens of μm from surfaces) of the water-absorbent resin.

The water-absorbent resin obtained in the present invention is favorable, because it has such a low water-extractable content and such a high absorption capacity that excellent surface-crosslinking effects are made on this water-absorbent resin, which therefore can display still higher properties and performances.

Herein, the "surface-crosslinking" means further forming a portion having high crosslinking density in surface layers of the resin besides a uniformly crosslinked structure inside the resin, and is carried out with the below-mentioned surface-crosslinking agent. The surface-crosslinking may be done by coating or impregnating the surface of the resin with the surface-crosslinking agent. The water absorption capacity under a load (AAP) and the saline flow conductivity (SFC) (liquid permeability under a load) are enhanced by surface-crosslinking the resin.

The water-absorbent resin according to the present invention favorably has a water absorption capacity of not less than 20 g/g, more favorably not less than 23 g/g, still more favorably not less than 25 g/g, for a physiological saline solution under a load (4.9 kPa). In addition, the process according to the present invention provides enablement for easy and stable production of a water-absorbent resin having high properties such that the absorption capacity for a physiological saline solution under a load (1.9 kPa) is also usually not less than 20 g/g, favorably not less than 25 g/g, more favorably not less than 28 g/g, particularly favorably not less than 32 g/g, and that the water absorption capacity without load is also not less than 25 g/g, more favorably not less than 28 g/g, particularly favorably not less than 32 g/g. In addition, the saline flow conductivity (SFC) (liquid permeability under a load) is favorably not less than $10 \times 10^{-7}$ ($cm^3 \cdot s \cdot g^{-1}$), more favorably not less than $20 \times 10^{-7}$ ($cm^3 \cdot s \cdot g^{-1}$), still more favorably not less than $50 \times 10^{-7}$ ($cm^3 \cdot s \cdot g^{-1}$).

In addition, the shape (particle diameter) and water-extractable content of the water-absorbent resin as finally obtained in the present invention are in their respective aforementioned ranges. Specifically, the shape is powdery and its weight-average particle diameter is favorably in the range of 100 to 1,000 μm, more favorably 200 to 600 μm, particularly favorably 300 to 500 μm, and further the quantity of particles having particle diameters in the range of 850 to 150 μm is favorably not less than 90 wt %, more favorably not less than 95 wt %, and further the water-extractable content is favorably not more than 25 wt %, more favorably not more than 15 wt %, still more favorably not more than 10 wt %.

In addition, as is specified in the below-mentioned description of examples of some preferred embodiments of the present invention and in the aforementioned object of the present invention, the water-absorbent resin according to the present invention has low coloring, little or no yellowing and a low residual monomer content. Specifically, its colored state indicates a YI value (Yellow Index/refer to EP 0942014 and EP 1108745) favorably in the range of 0 to 15, more favorably 0 to 13, still more favorably 0 to 10, most favorably 0 to 5, so there is almost no tinge of yellow. Furthermore, the residual monomer content is favorably not more than 400 ppm by weight, more favorably not more than 300 ppm by weight.

That is to say, the present invention further provides a novel water-absorbent resin, which is a crosslinked water-absorbent resin obtained by the process including the step of polymerizing a monomer component including acrylic acid and/or its salt in a major proportion, with the water-absorbent resin displaying an absorption capacity of not less than 20 g/g under a load (4.9 kPa or 1.9 kPa, favorably 4.9 kPa) and/or a saline flow conductivity of not less than $20 \times 10^{-7}$ ($cm^3 \cdot s \cdot g^{-1}$).

The water-absorbent resin according to the present invention favorably satisfies both the water absorption capacity under a load (AAP) and the saline flow conductivity (SFC), and more favorably further satisfies the above shape (particle diameter) and properties (absorption capacity, water-extractable content, residual monomer content, YI value). Such a water-absorbent resin is, for example, obtained by the aforementioned and below-mentioned production processes according to the present invention. As is aforementioned, the object of the present invention is to produce inexpensively with high productivity a water-absorbent resin of which the residual monomer content and the water-extractable content are both low, and the properties are high, and the colorability is low. In other words, the production processes according to the present invention produce the aforementioned water-absorbent resin.

Various crosslinking agents are usable for carrying out the above surface-crosslinking. However, from the viewpoint of the properties, examples thereof as generally used include: polyhydric alcohol compounds; epoxy compounds; polyamine compounds or their condensation products with haloepoxy compounds; oxazoline compounds; mono-, di-, or polyoxazolidinone compounds; polyvalent metal salts; and alkylene carbonate compounds.

The surface-crosslinking agent as used in the present invention is specifically exemplified in such as U.S. Pat. Nos. 6,228,930, 6,071,976, and 6,254,990. Examples thereof include: polyhydric alcohol compounds such as mono-, di-, tri-, tetra-, or polyethylene glycol, monopropylene glycol, 1,3-propanediol, dipropylene glycol, 2,3,4-triniethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol; epoxy compounds such as ethylene glycol diglycidyl ether and glycidol; polyamine compounds such as ethylenediamine, diethylenetriamine, triethylenetetramine, tetraethylenepentamine, pentaethylenehexamine, polyethylenimine, and polyamidopolyamines; haloepoxy compounds such as epichlorohydrin, epibromohydrin and α-methylepichlorohydrin; condensation products between the above polyamine compounds and the above haloepoxy compounds; oxazolidinone compounds such as 2-oxazolidinone; and alkylene carbonate compounds such as ethylene carbonate. However, there is no particular limitation. Of these crosslinking agents, at least the polyhydric alcohols are used favorably for maximizing the effects of the present invention, and polyhydric alcohols having 2 to 10 carbon atoms, favorably 3 to 8 carbon atoms, are used.

The quantity of the surface-crosslinking agent as used depends upon factors such as the types of the compounds used and combinations thereof, but is favorably in the range of 0.001 to 10 parts by weight, more favorably 0.01 to 5 parts by weight, per 100 parts by weight of the solid content of the resin.

In the present invention, water is favorably used for the surface-crosslinking. The quantity of water, as used on this occasion, depends upon the water content of the water-absorbent resin as used, but is usually in the range of favorably 0.5 to 20 parts by weight, more favorably 0.5 to 10 parts by weight, per 100 parts by weight of the water-absorbent resin. In addition, in the present invention, a hydrophilic organic solvent may be used as an alternative to water. The quantity of the hydrophilic organic solvent, as used on this occasion, is usually in the range of favorably 0 to 10 parts by weight, more favorably 0 to 5 parts by weight, still more favorably 0 to 3 parts by weight, per 100 parts by weight of the water-absorbent resin. The temperature of the crosslinking agent solution is favorably set in the range of 0° C. to boiling point, more favorably 5 to 50° C., still more favorably 10 to 30° C., from the viewpoint of the mixability and stability. In addition, before mixing, the temperature of the water-absorbent resin powder is favorably in the range of 0 to 80° C., more favorably 40 to 70° C., from the viewpoint of the mixability.

Furthermore, in the present invention, one preferred mixing method is a method including the steps of premixing the surface-crosslinking agent with water and/or the hydrophilic organic solvent, if necessary, and then spraying or dropwise adding (preferably, spraying) the resultant aqueous solution to the water-absorbent resin to mix them together. The size of the liquid droplets as sprayed is favorably not larger than 300 μm, more favorably not larger than 200 μm. In addition, in the mixing step, there may be allowed to coexist water-insoluble fine-particulate powders and/or surfactants within the range not damaging the effects of the present invention, for example, within the range of not more than 10 wt %, favorably not more than 5 wt %, more favorably not more than 1 wt %, relative to the water-absorbent resin.

A favorable mixing apparatus as used for the aforementioned mixing step needs to be able to generate great mixing power to ensure homogeneous mixing. Various mixing machines are usable in the present invention, but favorably they are high-speed agitation type mixers, particularly favorably, high-speed agitation type continuous mixers. Suitable mixers, for example, are available under the trade names: Turbulizer (produced by Hosokawa Milkron Co., Ltd. of Japan), and Lödige Mixer (produced by Gebrüder Lödige Maschinenbau GmbH of Germany).

After mixing with the surface-crosslinking agent, the resulting water-absorbent resin preferably is subjected to the heating treatment. As to conditions for carrying out the above heating treatment, the heating temperature is favorably in the range of 100 to 250° C., more favorably 150 to 250° C. The heating time is favorably in the range of 1 minute to 2 hours. Favorable examples of combinations of the temperature and time include: 180° C., 0.1 to 1.5 hours; and 200° C., 0.1 to 1 hour.

The heating treatment can be carried out by using conventional dryers or heating-furnaces. Examples of the dryers include channel type blending dryers, rotary dryers, disk dryers, fluidized-bed dryers, gas blowing type (pneumatic type) dryers, and infrared dryers. In addition, after being heated, the water-absorbent resin may be cooled, if necessary.

Incidentally, these surface-crosslinking methods are also disclosed in: various European patents such as EP 0349240, EP 0605150, EP 0812873, EP 0450924, and EP 0668080; various Japanese patents such as JP-A-242709/1995 and JP-A-224204/1995; various U.S. patents such as U.S. Pat. Nos. 5,409,771, 5,597,873, 5,385,983, 5,610,220, 5,633, 316, 5,672,633, and 5,462,972; and various international patent publications such as WO 99/42494, WO 99/43 720, and WO 99/42496. These surface-crosslinking methods are also applicable to the present invention.

(6) Uses of water-absorbent resin according to present invention:

It is also possible to provide various functions to the water-absorbent resin according to the present invention by further adding thereto materials, such as disinfectants, antimicrobial agents, perfumes, various inorganic powders, foaming agents, pigments, dyes, hydrophilic short fibers, manure, oxidants, reducing agents, water, and salts, favorably in a quantity of not larger than 20 parts by weight, more favorably not larger than 10 parts by weight, halfway through and/or after the production process. Examples of compounds that can be favorably added include water-insoluble inorganic powders and/or polyamines.

The process according to the present invention provides the easy production of a water-absorbent resin having good absorption properties in excellent balance between the absorption capacity without load, the absorption capacity under a load, and the extractable content. The resulting water-absorbent resin is widely used for various purposes such as agricultural and horticultural water-retaining agents, industrial water-retaining agents, humidity-absorbing agents, dehumidifying agents, and building materials, but the water-absorbent resin according to the present invention is particularly favorably used for sanitary materials such as disposable diapers, incontinent pads, mother's breast pads (nursing pads), and sanitary napkins.

Furthermore, the water-absorbent resin according to the present invention is so excellent with regard to the above three properties being in good balance that the water-absorbent resin can be used in the sanitary materials (particularly, disposable diapers) in high concentrations where the water-absorbent resin concentration (weight ratio of the water-absorbent resin to the total weight of the water-absorbent resin and fibrous materials), is preferably 30 to 100 wt %, more favorably 40 to 100 wt %, still more favorably 50 to 95 wt %.

DETAILED DESCRIPTION OF PREFERRED EMBODIMENTS

Hereinafter, the present invention is more specifically illustrated by the following examples of some preferred embodiments of the present invention in comparison with comparative examples not according to the invention. However, this should not be interpreted as limiting the present invention to these examples. In addition, the properties, as recited in the claims of the present invention and in the examples of some preferred embodiments of the present invention, were determined by the following measurement methods.

(1) Absorption capacity (TB) of water-absorbent resin for physiological saline solution:

The absorption capacity without load was determined in accordance with U.S. Pat. No. 5,164,459. Specifically, 0.2 g of water-absorbent resin was uniformly placed into a non-woven-fabric-made bag resembling a tea bag (40×150 mm). The bag was sealed and then immersed into 100 g of a 0.9 wt % aqueous sodium chloride solution (physiological saline solution) of 25(±3)° C. Thirty minutes later, the bag was withdrawn from the physiological saline solution and then drained of water, and the resultant weight M1 of the bag was then measured. On the other hand, the same procedure as the above was carried out without the water-absorbent resin, and the resultant weight M2 of the empty bag was determined. Thus, the absorption capacity was calculated in accordance with the following equation:

Absorption capacity $(g/g)$=(weight after absorption $M1(g)$–blank weight $M2(g)$/weight$(g)$ of water-absorbent resin (2) Absorption capacity (GVj) of water-absorbent resin for artificial urine:

The absorption capacity without load was determined in accordance with U.S. Pat. No. 5,164,459. Specifically, 0.2 g of water-absorbent resin was uniformly placed into a non-woven-fabric-made bag (60×60 mm). The bag was sealed and then immersed into 100 g of artificial urine of 25(±3)° C. Sixty minutes later, the bag was withdrawn and then drained of liquid at 250 G with a centrifuge for 3 minutes, and the resultant weight M1 of the bag was then measured. On the other hand, the same procedure as the above was carried out without the water-absorbent resin, and the resultant weight M2 of the empty bag was determined. Thus, the absorption capacity was calculated in accordance with the equation of (1) above.

Incidentally, the artificial urine that was used is what is called Jayco artificial urine (USA: available from Jayco, Inc.) (composition: solution of 2.0 g of potassium chloride, 2.0 g of sodium sulfate, 0.85 g of ammonium dihydrogenphosphate, 0.15 g of diammonium monohydrogenphosphate, 0.19 g of calcium chloride, and 0.23 g of magnesium chloride all as anhydrous salts in 1 liter of distilled water).

(3) Water-extractable content (which may be abbreviated to extractable content):

First, 500 mg of water-absorbent resin was dispersed into 1,000 ml of deionized water of room temperature and then stirred with a magnetic stirrer of 40 mm for 16 hours. Then, the resultant swollen gel was filtered off with a filter paper (TOYO, No. 6). Next, a water-soluble polymer, which had eluted from the water-absorbent resin into the resultant filtrate, was quantified by colloidal titration, thereby determining the wt % as the water-extractable content (relative to water-absorbent resin) of the water-absorbent resin.

(4) Residual monomer content:

The residual monomer content of the water-absorbent resin powder, after drying, was determined in the following way. In (3) above, a filtrate, as separately prepared after stirring for 2 hours, was UV-analyzed by liquid chromatography to also analyze the residual monomer content ppm (relative to water-absorbent resin) of the water-absorbent resin.

In addition, the residual monomer content of the hydrogel, before drying, was determined by: stirring a finely disintegrated hydrogel of about 500 mg in solid resin content for 16 hours; and then UV-analyzing its filtrate by liquid chromatography likewise; and then correcting the solid content.

(5) Absorption capacity under load (AAP):

The absorption capacity for a physiological saline solution under a load was measured by the methods disclosed in U.S. Pat. Nos. 6,226,930, 6,071,976, and 6,254,990.

In accordance with the methods as disclosed in the aforementioned U.S. patents, 900 Mg of water-absorbent resin was allowed to absorb a physiological saline solution over a period of 60 minutes in a state where a predetermined load (1.9 kPa or 4.9 kPa) was applied to the water-absorbent resin, and then the weight of the absorbed physiological saline solution was determined from a value as measured with a balance. Separately, the same procedure as the above was carried out without the water-absorbent resin, whereby the weight of the physiological saline solution 11 as absorbed by materials other than the water-absorbent resin, for example, the filter paper 7, was determined as a blank value from a value as measured with the balance 1. Next, correction was made by subtracting this blank value from the aforementioned measured value, and then the resultant weight of the physiological saline solution 11 as actually absorbed by the water-absorbent resin was divided by the weight of the water-absorbent resin (0.9 g), thus calculating the absorption capacity (g/g) under a load of 1.9 kPa or 4.9 kPa.

(6) Saline flow conductivity (SFC) (liquid permeability under load):

The method for measuring the saline flow conductivity (liquid permeability under a load) was carried out in accordance with WO 95/22356. Specifically, 0.9 g of water-absorbent resin was swollen under a load of 20 g/cm$^2$ (about 1.9 kPa) for 1 hour, and then the saline flow conductivity (abbreviated as SFC) of the resultant swollen gel to a 0.0018M-NaCl solution (20–25° C.) under a load of 20 g/cm$^2$ (about 1.9 kPa) was determined. Incidentally, its unit was (cm$^3$·s·g$^{-1}$). The larger this numerical value is, the greater the liquid permeability is.

(7) Peak time and induction time:

The temperature of the monomer or of the resultant polymer gel during the polymerization was measured with a thermometer, and the time (minutes) of from addition of initiator until a rise of temperature was defined as the induction time. The time until the maximum temperature of the polymerization system is attained was defined as the peak time.

(8) Quantification of p-methoxyphenol:

UV analysis was carried out by liquid chromatography.

(9) Weight-average particle diameter (D50):

The water-absorbent resin powder or water-absorbing agent was classified by sieving with JIS standard sieves having mesh opening sizes of such as 850 μm, 600 μm, 500 μm, 300 μm, and 150 μm, and then the percentages of the residues on these sieves, R, were plotted on logarithmic probability paper. Therefrom, the weight-average particle diameter (D50) was read.

The classification method was as follows. Under conditions of a room temperature (20 to 25° C.) and a humidity of 50 RH%, 10.0 g of water-absorbent resin powder or water-absorbing agent was placed onto JIS standard sieves (having mesh opening sizes of 850 μm, 600 μm, 500 μm, 300 μm, and 150 μm) (THE IIDA TESTING SIEVE: diameter=8 cm), and then classified with a sieve shaker (IIDA SIEVE SHAKER, TYPE: ES-65 type, SER. No. 0501) for 10 minutes.

(10) Evaluation of coloring of water-absorbent resin (YI value):

This was carried out in accordance with EP 0942014 and EP 1108745. Specifically, the evaluation of coloring of the water-absorbent resin powder was carried out in the following way using a spectroscopic color difference meter (SZ-Σ80 COLOR MEASURING SYSTEM, produced by Nippon Densholcu Kogyo Co., Ltd.). About 6 g of the water-absorbent resin was filled into the below-mentioned powder-paste sample stand (filling of about 60 % of this sample stand) to measure the surface color (YI value (Yellow Index)) of the water-absorbent resin using the above spectroscopic color difference meter under its set conditions (reflection measurement/appendix powder-paste sample stand (inner diameter: 30 mm)/standard round white board No. 2/30 mm φ projector pipe for powder-paste as the standard) under conditions of a room temperature (20 to 25° C.) and a humidity of 50 RH%.

In addition, color difference (L, a, b) or WB (Hunter Color) which is another yardstick is also measurable at the same time by the same method with the same apparatus as the above. The larger L/WB and the smaller a/b indicate that die coloring is lower and that the color is nearer to being substantially white.

(11) Protoanemonin content and furfural content:

These were quantitatively analyzed on the basis of standard samples with a gas chromatograph (GC-7A model, produced by Shimadzu Corporation) and a data processor (C-R6A model, produced by Shimadzu Corporation) under the following conditions: Detector: FID Quantity of hydrogen: 30 m/min Quantity of air: 0.5 L/min Column: Hard glass tube of 3 mm in inner diameter and 3.1 m in length Filler: Chromosorb W Temperature of column incubator: 100° C.

Temperature of sample-injecting part: 150° C.

Flow rate of carrier gas: nitrogen 40 mL/min

(12) Light resistance:

First, 1.0 g of water-absorbent resin was swollen to 100 times with ion-exchanged water, and then sealed in a glass mayonnaise bottle, and then left alone outdoors in fine summer weather for a whole day. Then, the state of the swollen gel was visually observed, and further, the water-extractable content of the swollen gel was measured by the above method (3).

(13) Urine resistance:

First, 1.0 g of water-absorbent resin was swollen to 25 times with an adult's urine, and then sealed in a bottle of 100 ml, and then left alone under a constant temperature of 37° C. After 16 hours, the state of the swollen gel was observed with the eye, and further, the bottle was tilted to measure a flowing distance of the gel.

PRODUCTION EXAMPLE 1

Production of Acrylic Acid Composition (1):

Commercially available acrylic acid (special-grade reagent available from Wako Pure Chemical Industries, Ltd.; p-methoxyphenol content=200 ppm by weight), as obtained by catalytic gas phase oxidation, was supplied into the column bottom of a high-boiling-point-impurities-separating column having fifty dual-flow perforated plates, and then distilled in a reflux ratio of 1 and then further re-distilled, thus obtaining an acrylic acid composition (1) comprising acrylic acid at a concentration of not less than 99 % and only trace amounts of impurities (mainly, water). This acrylic acid composition (1) had a p-methoxyphenol content of ND (less than 1 ppm by weight) and also a protoanemonin content of ND (less than 1 ppm by weight) and also a furfural content of ND (less than 1 ppm by weight). Incidentally, this Production Example 1 is a comparative example as well as a production example of an acrylic acid composition.

PRODUCTION EXAMPLES 2 TO 6

Production of Acrylic Acid Compositions (2) to (6):

Acrylic acid compositions (2) to (6) having their respective predetermined p-methoxyphenol contents were obtained by adding p-methoxyphenol, in quantities of 20 ppm by weight, 25 ppm by weight, 50 ppm by weight, 70 ppm by weight, and 200 ppm by weight respectively (relative to solid content of acrylic acid), to the acrylic acid composition (1) as obtained in Production Example 1. Incidentally, these Production Examples 2 to 6 are working-examples as well as production examples of acrylic acid compositions.

PRODUCTION EXAMPLE 7

Production of Aqueous Sodium Acrylate Solution (1):

A five-necked flask of 5 liters, as equipped with two dropping funnels, a pH meter, a thermometer, and stirring blades, was charged with 1,598 g of ion-exchanged water. In addition, separately, 1,280 g of the acrylic acid composition (1) (consisting substantially of acrylic acid) at room temperature and 1,488 g of 48 wt % aqueous sodium hydroxide solution at room temperature were placed into the two dropping funnels respectively, and the flask of 5 liters was immersed into a water-cooling bath.

Next, while the temperature of the neutralization reaction system in the flask of 5 liters was maintained at not higher than 35° C. under stirred conditions, the 48 wt % aqueous sodium hydroxide solution and the acrylic acid composition (1) were dropwise added into the flask at the same time as each other. The dropwise addition of the acrylic acid composition (1) was completed in about 35 minutes, and the dropwise addition of the 48 wt % aqueous sodium hydroxide solution was completed in about 45 minutes. After the completion of the dropwise addition of the acrylic acid composition (1), its dropping funnel was washed with 100 g of ion-exchanged water, and all the used washing water was then added into the flask. Furthermore, after the completion of the dropwise addition of the 48 wt % aqueous sodium hydroxide solution, its dropping funnel was similarly washed with 100 g of ion-exchanged water, and all the used washing water was then added into the flask.

After the completion of all the dropwise additions, the temperature was adjusted into the range of 20–35° C. to age the reaction mixture for 20 minutes. After this aging, an extremely small quantity of the acrylic acid composition (1) was dropwise added to adjust the pH to 10 (±0.1), thus obtaining an aqueous sodium acrylate solution (1) having a monomer concentration of 37 wt % and a neutralization of 100 mol %.

PRODUCTION EXAMPLES 8 to 11

Production of Aqueous Sodium Acrylate Solutions (3) to (6):

Neutralization was carried out in the same ways as of the above production of the aqueous sodium acrylate solution (1) except that the acrylic acid composition (1) as used for the neutralization was replaced with the acrylic acid compositions (3) to (6) having their respective predetermined p-methoxyphenol contents of 25–200 ppm by weight, thus obtaining an aqueous sodium acrylate solution (3) from the acrylic acid composition (3) having a p-methoxyphenol content of 25 ppm by weight, an aqueous sodium acrylate solution (4) from the acrylic acid composition (4) having a p-methoxyphenol content of 50 ppm by weight, an aqueous sodium acrylate solution (5) from the acrylic acid composition (5) having a p-methoxyphenol content of 70 ppm by weight, and an aqueous sodium acrylate solution (6) from the acrylic acid composition (6) having a p-methoxyphenol content of 200 ppm by weight.

PRODUCTION EXAMPLES 12 to 16

Production of Aqueous Sodium Acrylate Solutions (1-2), (3-2) to (6-2):

A quantity of 3.92 g of active carbon was added to the entirety of the aqueous sodium acrylate solution (1) as obtained in Production Example 7, and then the resultant active-carbon-dispersed aqueous sodium acrylate solution (1) was stirred for 30 minutes, and then the active carbon was suction-filtered off with a filter paper (No. 2, produced by Advantech Toyo K.K.) to obtain an aqueous sodium acrylate solution (1-2) having a turbidity of 0.3.

In addition, the aqueous sodium acrylate solutions (3) to (6), as obtained in Production Examples 8 to 11, were also likewise treated with active carbon to obtain aqueous sodium acrylate solutions (3-2) to (6-2) respectively having a turbidity of 0.3.

PRODUCTION EXAMPLE 17

Production of Acrylic Acid Composition (7):

Commercially available acrylic acid, as obtained by catalytic gas phase oxidation, was distilled with an Oldershaw column type distillation apparatus of 32φ and 2 stages. Its distillation column has a condenser, a distillate-extracting tube, and a reflux-supplying tube at a top portion of the column and further has a boiler, a raw-material-liquid-supplying tube, and an oxygen-supplying tube at a lower portion of the column, wherein the condenser has a stabilizing-agent-supplying tube at its upper portion.

Commercially available acrylic acid having a p-methoxyphenol content of 200 ppm by weight was used as the raw material liquid, and this raw material liquid was supplied at 295 ml/hour from the lower portion of the column. Acrylic acid distilled from the column top was supplied from the column top in a reflux ratio of 0.99. The distillation column was operated under an operational pressure of 95 hPa, a column top temperature of 77° C., and a column bottom temperature of 82° C. In this operation, a solution in the reflux having a p-methoxyphenol content of 50 ppm by weight relative to the vapor quantity at the column top was added from the stabilizing-agent-supplying tube of the upper portion of the condenser. In addition, molecular oxygen of a ratio of 0.18 volume % relative to the vapor quantity at the column top was added from the column bottom of the distillation column.

As a result of the distillation of the acrylic acid under the above conditions, an acrylic acid composition (7) having a protoanemonin content of ND (not detectable) (less than 1 ppm by weight) and a p-methoxyphenol content of 55 ppm by weight was obtained at a rate of 292 ml/hour from the distillate-extracting tube during the stationary operation. Incidentally, this Production Example 17 is a working example as well as a production example of an acrylic acid composition.

PRODUCTION EXAMPLE 18

Production of Acrylic Acid Composition (8):

The distillation of the acrylic acid was carried out in the same way as the above Production Example 17 except for not carrying out the addition of p-methoxyphenol from the stabilizing-agent-supplying tube.

Acrylic acid (an acrylic acid composition (8)) was obtained at a rate of 292 ml/hour from the distillate-extracting tube during the stationary operation. However, the resultant acrylic acid had a protoanemonin content of ND (less than 1 ppm by weight) and a p-methoxyphenol content of ND (less than 1 ppm by weight). Incidentally, this Production Example 18 is a comparative example as well as a production example of an acrylic acid composition.

PRODUCTION EXAMPLE 19

Production of Acrylic Acid Composition (9):

Acrylic acid was treated with such an apparatus as disclosed in JP-B-041637/1978. Specifically, commercially available acrylic acid was treated with a crystallizer having a metal tube of the length of 6 m and the inner diameter of 70 mm which was provided with a reservoir at a lower portion and of which the surface was covered with a double jacket wherein the crystallizer had a mechanism such that a liquid could be fed from the reservoir to an upper portion of the tube with a circulating pump and then allowed to flow in the form of a falling film on an inner surface of the tube.

Commercially available acrylic acid having a p-methoxyphenol content of 200 ppm by weight was used as the raw material liquid, and this acrylic acid was supplied to the reservoir and then allowed to flow in the form of a falling film on the inner surface of the tube by the circulating pump. The temperature of the jacket was lowered to not higher than the solidifying point to crystallize about 80 wt % on the inner surface. Then, the circulating pump was stopped, and the temperature of the jacket was raised near the solidifying point to melt about 2 wt %, and then the resultant melted liquid was extracted with a pump.

The temperature of the jacket was further raised to not lower than the solidifying point to melt the crystal, thus obtaining an acrylic acid composition (9) having a protoanemonin content of ND (less than 1 ppm by weight), a furfural content of ND (less than 1 ppm by weight), and a p-methoxyphenol content of 30 ppm by weight. Incidentally, this Production Example 19 is a working example as well as a production example of an acrylic acid composition.

PRODUCTION EXAMPLE 20

Production of Acrylic Acid Composition (10):

A reaction gas, as obtained by catalytic gas phase oxidation of propylene, was collected into water in an absorption column to obtain an aqueous acrylic acid solution. Next, this aqueous acrylic acid solution was supplied into a solvent-separating column to distill off water and low-boiling-point impurities such as acetic acid with an azeotropic solvent, and then supplied into the column bottom of a high-boiling-point-impurities-separating column having twenty dual-flow perforated plates, and then distilled in a reflux ratio of 2, and then subjected to addition of p-methoxyphenol of an amount of 50 ppm by weight, thus obtaining an acrylic acid composition (10) from the column top. This acrylic acid composition (10) had a p-methoxyphenol content of 50 ppm by weight, a protoanemonin content of 30 ppm by weight and a furfural content of 50 ppm by weight.

PRODUCTION EXAMPLE 21

Production of Acrylic Acid Composition (11):

A reaction gas, as obtained by catalytic gas phase oxidation of propylene, was collected into water in an absorption column to obtain an aqueous acrylic acid solution. Next, this aqueous acrylic acid solution was supplied into a solvent-separating column to distil off water and low-boiling-point impurities such as acetic acid with an azeotropic solvent, and then supplied into the column bottom of a high-boiling-point-impurities-separating column having fifty dual-flow perforated plates, and then distilled in a reflux ratio of 2. When this distillation with the high-boiling-point-impurities-separating column was carried out, p-methoxyphenol was added from an upper portion of a condenser of the high-boiling-point-impurities-separating column, and also, hydrazine hydrate was added onto a tray of the 25th stage from the bottom of the high-boiling-point-impurities-separating column, thus obtaining from the column top an acrylic acid composition (11) having a p-methoxyphenol content of 50 ppm by weight, a protoanemonin content of ND (less than 1 ppm by weight) and a furfural content of ND (less than 1 ppm by weight).

PRODUCTION EXAMPLE 22

Production of Acrylic Acid Composition (12):

A reaction gas, as obtained by catalytic gas phase oxidation of propylene, was collected into water in an absorption column to obtain an aqueous acrylic acid solution. Next, this aqueous acrylic acid solution was supplied into a solvent-separating column to distil off water and low-boiling-point impurities such as acetic acid with an azeotropic solvent while p-methoxyphenol was added as a polymerization inhibitor from the column top in the form of a solution in the azeotropic solvent. Thereafter, the column bottom liquid in the solvent-separating column was treated with such an apparatus as disclosed in JP-B-041637/1978. Specifically, the column bottom liquid was treated with a crystallizer having a metal tube of the length of 6 m and the inner diameter of 70 mm which was provided with a reservoir at a lower portion and of which the surface was covered with a double jacket wherein the crystallizer had a mechanism such that a liquid could be fed from the reservoir to an upper portion of the tube with a circulating pump and then allowed to flow in the form of a falling film on an inner surface of the tube.

The column bottom liquid was supplied to the reservoir and then allowed to flow in the form of a falling film on the inner surface of the tube by the circulating pump. The temperature of the jacket was lowered to not higher than the solidifying point to crystallize about 70 wt % on the inner surface. Then, the circulating pump was stopped, and the temperature of the jacket was raised to not lower than the solidifying point to melt the crystal, thus obtaining a treated liquid from the column bottom liquid. This treated liquid was then subjected to the above crystallization step again, thus carrying out the crystallization treatment two times in total. As a result, there was obtained an acrylic acid composition (12) having a p-methoxyphenol content of 15 ppm by weight, a protoanemonin content of ND (less than 1 ppm by weight) and a furfural content of ND (less than 1 ppm by weight).

(Production of Water-absorbent Resins):

Hereinafter, influences of p-methoxyphenol upon polymerization in producing water-absorbent resins were examined with acrylic acid compositions (acrylic acids) having a protoanemonin content of ND (less than 1 ppm by weight) and a furfural content of ND (less than 1 ppm by weight). Incidentally, only in Example 28, there was used an acrylic acid composition (acrylic acid) having a protoanemonin content of 30 ppm by weight.

Example 1 and Comparative Examples 1 and 2 are acid polymerization processes in which acrylic acid having a neutralization amount of 0 mol % is polymerized and, after this polymerization, neutralization is carried out. The other Examples and Comparative Examples are neutralization polymerization processes in which beforehand neutralized acrylic acid is polymerized. Their results are shown in Tables 1 and 2.

The results of the surface-crosslinking are shown in Table 3.

Influences of hydrogen peroxide and the neutralization ratio upon the polymerization are shown in Table 4.

Shown in FIG. 1 is generation of heat (temperature of polymerization system) with the passage of time during the polymerization in Example 1 and Comparative Examples 1 and 2.

Incidentally, in the following examples of some preferred embodiments of the polymerization in the present invention, unless otherwise noted, the above aqueous sodium acrylate solutions resultant from the neutralization were used for preparation of aqueous monomer solutions within 30 minutes after the neutralization, and further the resultant aqueous monomer solutions were used for the polymerization within 30 minutes after their preparation. In addition, the crosslinked hydrogel polymers resultant from the polymerization were placed into dryers within 5 minutes after being removed from the polymerization containers. Although being shown also in Examples 29 and 30 below, it is aforementioned that, as these times become longer, it becomes more difficult to achieve the reduction of the residual monomer content and the low coloring.

EXAMPLE 1

A cylindrical polypropylene container of 1 liter in capacity with a lid was prepared as a polymerization container.

An aqueous monomer solution (1) having a p-methoxyphenol content of 20 ppm by weight, a monomer concentration of 20 wt % and a neutralization ratio of 0 mol % was obtained by mixing together 72.07 g of the acrylic acid composition (2) (being obtained in Production Example 2 and having a p-methoxyphenol content of 20 ppm by weight), 293.06 g of ion-exchanged water, and polyethylene glycol diacrylate (molar-number-average degree "n" of addition polymerization of ethylene oxide=8.2) as an internal-crosslinking agent in an amount of 0.05 mol % (to the entire monomers). Furthermore, while being kept at 20° C., this aqueous monomer solution (1) was charged into the above cylindrical container, and then nitrogen gas was introduced into the solution to deaerate the solution with nitrogen gas to reduce its dissolved oxygen content to not more than 1 ppm.

Next, while the cylindrical container was thermally insulated in an adiabatic state, a polymerization initiator, comprising a combination of an aqueous solution of sodium persulfate (of the ratio of 0.12 g/(mol of entire monomers) (hereinafter abbreviated to g/mol)) with an aqueous solution of L-ascorbic acid (of the ratio of 0.0018 g/mol), was added to the aqueous monomer solution (1) to initiate static polymerization. After a certain time, the polymerization started and then was allowed to proceed and then, after having reached the peak temperature, the polymerization was continued for another 30 minutes, thus obtaining a cylindrical crosslinked hydrogel polymer. The resultant crosslinked hydrogel polymer was finely disintegrated into pieces of the size of about 1 mm, and then thereto 62.5 g of 48 wt % aqueous sodium hydroxide solution was added to neutralize 75 mol % of acid groups of the polymer. With regard to the neutralized crosslinked hydrogel polymer (1) as obtained in the above way, the polymerization conversion was 98.4 % (the residual monomer content was 16,000 ppm by weight).

Next, the above hydrogel was spread onto a metal gauze of 850 µm, and then hot-wind-dried with a gas of 160° C. (dew point: 60° C.) for 60 minutes, and then pulverized with a vibration mill, and further then classified with a JIS standard sieve of 850 µm, thus obtaining a water-absorbent resin powder (1).

COMPARATIVE EXAMPLE 1

A comparative aqueous monomer solution (1) was prepared in the same way as of Example 1 except that, as the monomer, the acrylic acid composition (2) was replaced with the acrylic acid composition (1) having a p-methoxyphenol content of ND (less than 1 ppm by weight). Thereafter, in the same way as of Example 1, the comparative aqueous monomer solution (1) was polymerized and then neutralized. With regard to a comparative neutralized crosslinked hydrogel polymer (1) as obtained in the above way, the polymerization conversion was 93.0 % (the residual monomer content was 70,000 ppm by weight). Thereafter, this polymer was dried, pulverized, and classified in the same way as of Example 1, thus obtaining a comparative water-absorbent resin powder (1).

COMPARATIVE EXAMPLE 2

A comparative aqueous monomer solution (2) was prepared in the same way as of Example 1 except that as the monomer, the acrylic acid composition (2) was replaced with the acrylic acid composition (6) having a p-methoxyphenol content of 200 ppm by weight. Thereafter, in the same way as of Example 1, the comparative aqueous monomer solution (2) was polymerized and then neutralized.

With regard to the resultant comparative neutralized crosslinked hydrogel polymer (2), the polymerization conversion was 96.7 % (the residual monomer content was 33,000 ppm by weight). Thereafter, this polymer was dried, pulverized, and classified in the same way as of Example 1, thus obtaining a comparative water-absorbent resin powder (2).

EXAMPLE 2

A jacketed stainless-steel-made twin-arm kneader of 10 liters in capacity of which the internal surface had been coated with a fluororesin (Teflon) was prepared as a polymerization container. This kneader is equipped with two sigma type blades of 120 mm in rotational diameter and a lid for sealing up the inside of the system.

An aqueous monomer solution (2) having a monomer concentration of 37 wt % and a neutralization ratio of 75 mol % was obtained by mixing together 376.3 g of the acrylic acid composition (3) (being obtained in Production Example 3 and having a p-methoxyphenol content of 25 ppm by weight) and 3,983 g of its neutralized product, namely, the aqueous sodium acrylate solution (3), and further, 640.7 g of ion-exchanged water, and trimethylolpropane triacrylate as an internal-crosslinking agent in a ratio of 0.045 mol % (to the entire monomers). Furthermore, while being kept at 22° C., this aqueous monomer solution (2) was charged into the sigma type twin-arm kneader, and then nitrogen gas was introduced into the solution to deaerate the solution with nitrogen gas to reduce its dissolved oxygen content to not more than 1 ppm.

Next, while warm water was passed through the jacket and while the aqueous monomer solution (2) was stirred, a polymerization initiator, comprising a combination of an aqueous solution of sodium persulfate (in an amount of 0.09 g/mol) with an aqueous solution of L-ascorbic acid (in an amount of 0.005 g/mol), was added to the aqueous monomer solution (2) to initiate polymerization. After a certain time, the polymerization started and then was allowed to proceed while the resultant polymer gel was disintegrated into fine pieces, and then, after having reached the peak temperature, the polymerization was continued for another 20 minutes, thus obtaining a finely-disintegrated crosslinked hydrogel polymer (2) having diameters in the range of about 1 to about 2 mm.

The resultant hydrogel polymer (2) was spread onto a metal gauze of 850 µm and then hot-wind-dried at 150° C. (dew point: 50° C.) for 90 minutes. Next, the resultant dried product was pulverized with a vibration mill, and further then classified with a JIS standard sieve of 850 µm, thus obtaining a water-absorbent resin powder (2).

EXAMPLE 3

Polymerization was carried out in the same way as in Example 2 except that, as the monomers, the acrylic acid composition (3) and the aqueous sodium acrylate solution (3) were replaced with the acrylic acid composition (4) (having a p-methoxyphenol content of 50 ppm by weight) and its neutralized product, namely, the aqueous sodium acrylate solution (4). Thereafter, the resultant polymer was dried, pulverized, and classified in the same way as in Example 2, thus obtaining a water-absorbent resin powder (3).

COMPARATIVE EXAMPLE 3

Polymerization was carried out in the same way as in Example 2 except that, as the monomers, the acrylic acid composition (3) and the aqueous sodium acrylate solution (3) were replaced with the acrylic acid composition (1) (having a p-methoxyphenol content of ND (less than 1 ppm by weight)) and its neutralized product, namely, the aqueous sodium acrylate solution (1). Thereafter, the resultant polymer was dried, pulverized, and classified in the same way as in Example 2, thus obtaining a comparative water-absorbent resin powder (3).

EXAMPLE 4

Polymerization was carried out in the same way as in Example 2 except that, as a monomer, the aqueous sodium acrylate solution (3) was replaced with what was obtained by further treating this neutralized product with active carbon, namely, the aqueous sodium acrylate solution (3-2). Thereafter, the resultant polymer was dried, pulverized, and classified in the same way as in Example 2, thus obtaining a water-absorbent resin powder (4).

EXAMPLE 5

Polymerization was carried out in the same way as in Example 3 except that, as a monomer, the aqueous sodium acrylate solution (4) was replaced with what was obtained by further treating this neutralized product with active carbon, namely, the aqueous sodium acrylate solution (4-2). Thereafter, the resultant polymer was dried, pulverized, and classified in the same way as in, Example 3, thus obtaining a water-absorbent resin powder (5).

COMPARATIVE EXAMPLE 4

Polymerization was carried out in the same way as in Comparative Example 3 except that, as a monomer, the aqueous sodium acrylate solution (1) was replaced with what was obtained by further treating this neutralized product with active carbon, namely, the aqueous sodium acrylate solution (1-2). Thereafter, the resultant polymer was dried, pulverized, aid classified in the same way as in Comparative Example 3, thus obtaining a comparative water-absorbent resin powder (4).

COMPARATIVE EXAMPLE 5

Polymerization was carried out in the same way as in Example 2 except that, as the monomers, the acrylic acid composition (3) and the aqueous sodium acrylate solution (3) were replaced with the acrylic acid composition (6) (having a p-methoxyphenol content of 200 ppm by weight) and what was obtained by further treating a neutralized product of this composition with active carbon, namely, the aqueous sodium acrylate solution (6-2). Thereafter, the resultant polymer was dried, pulverized, and classified in the same way as in Example 2, thus obtaining a comparative water-absorbent resin powder (5).

Hereinafter examined were influences of transition metals in the presence of p-methoxyphenol of a ratio of 50 ppm by weight. Their results are shown in Table 2, including the results of Examples 6 to 12.

EXAMPLE 6

Polymerization was carried out in the same way as in Example 5 except that the temperature (polymerization initiation temperature) of the aqueous monomer solution was changed from 22° C. into 15.5(±2)° C. Thereafter, the resultant polymer was dried, pulverized, and classified in the same way as in Example 5, thus obtaining a water-absorbent resin powder (6).

EXAMPLE 7

An aqueous monomer solution was prepared in the same way as in Example 6 except that Fe (I) ion (ferrous chloride) was added thereto in a quantity of 4 ppm by weight (relative to solid content of sodium acrylate/in terms of Fe). Thereafter, polymerization of the aqueous monomer solution containing the above-stated quantity of Fe (I) was carried out in the same way as in Example 6. Thereafter, the resultant polymer was dried, pulverized, and classified in the same way as in Example 6, thus obtaining a water-absorbent resin powder (7).

EXAMPLE 8

Polymerization was carried out in the same way as in Example 7 except that Fe (I) ion (ferrous chloride) was added to the aqueous monomer solution in a quantity of 0.4 ppm by weight. Thereafter, the resultant polymer was dried,

TABLE 1

| | p-Methoxyphenol content (ppm by weight) | Active carbon treatment (done or none) | Peak time (polymerization rate) (minutes) | Absorption capacity without load | | Extractable content (wt %) | Residual monomer content (ppm by weight) | Residual monomer content of hydrogel after polymerization (ppm by weight) | Coloring YI | Weight-average particle diameter D50 (μm) |
|---|---|---|---|---|---|---|---|---|---|---|
| | | | | TB Physiological saline solution (g/g) | GVj Artificial urine (g/g) | | | | | |
| Comparative Example 1 | 0 | None | 31 | 50 | 45 | 10 | 500 | 7.0 | 3.9 | 400 |
| Example 1 | 20 | None | 24 | 50 | 48 | 9 | 340 | 1.6 | 3.9 | 400 |
| Comparative Example 2 | 200 | None | 40 | 48 | 46 | 9 | 550 | 3.3 | 17.1 | 400 |
| Comparative Example 3 | 0 | None | 12 | 48 | 46 | 9.9 | 250 | — | 4.1 | 430 |
| Example 2 | 25 | None | 11 | 49 | 47 | 9.3 | 320 | — | 4.0 | 430 |
| Example 3 | 50 | None | 10 | 49 | 47 | 9.2 | 320 | — | 9.2 | 430 |
| Comparative Example 4 | 0 | Done | 20 | 48 | 46 | 7.4 | 170 | — | 3.8 | 430 |
| Example 4 | 25 | Done | 10 | 47 | 45 | 7.6 | 220 | — | 3.1 | 430 |
| Example 5 | 50 | Done | 10 | 46 | 45 | 8.4 | 190 | — | 5.1 | 430 |
| Comparative Example 5 | 200 | Done | 11 | 47 | 46 | 7.5 | 270 | — | 10.3 | 430 |
| Example 16 | 70 | None | 10 | 48 | 47 | 9.3 | 330 | — | 10.1 | 360 |
| Example 17 | 150 | None | 12 | 47 | 46 | 9.5 | 330 | — | 14.7 | 360 |
| Comparative Example 6 | 200 | None | 13 | 47 | 45 | 10 | 360 | — | 20.2 | 360 |
| Example 18 | 25 | None | 7 | 52 | 50 | 12 | 200 | — | 3.9 | 450 |
| Example 19 | 50 | None | 7 | 53 | 50 | 13 | 240 | — | 8.9 | 450 |
| Comparative Example 7 | 200 | None | 8 | 51 | 49 | 13 | 320 | — | 19.1 | 450 |

Note):
In any water-absorbent resin, the quantity of fine particles having particle diameters of not larger than 150 μm is in the range of 2 to 5 wt %.

pulverized, and classified in the same way as in Example 7, thus obtaining a water-absorbent resin powder (8).

EXAMPLE 9

Polymerization was carried out in the same way as in Example 7 except that Fe (I) ion (ferrous chloride) was added to the aqueous monomer solution in a quantity of 0.04 ppm by weight. Thereafter, the resultant polymer was dried, pulverized, and classified in the same way as in Example 7, thus obtaining a water-absorbent resin powder (9).

EXAMPLES 10 to 12

Polymerization was carried out in the same ways as in Example 7 except that, during the polymerization, the Fe (I) ion (ferrous chloride) was replaced with Cu ion (cuprous chloride), Mn ion (manganese chloride), and Ti ion (titanium trichloride) of a ratio of 0.4 ppm by weight each. Thereafter, the resultant polymers were dried, pulverized, and classified in the same ways as in Example 7, thus obtaining water-absorbent resin powders (10) to (12).

TABLE 2

| | Transition metal content (ppm by weight) | Induction time (minutes)/ peak time (minutes) | Absorption capacity without load | | Extractable content (wt %) | Residual monomer content (ppm by weight) | Coloring YI |
|---|---|---|---|---|---|---|---|
| | | | TB Physiological saline solution (g/g) | GVj Artificial urine (g/g) | | | |
| Example 6 | None | 2.1/12.7 | 43 | 42 | 8.6 | 290 | 9.0 |
| Example 7 | Fe = 4 | 0.2/17.8 | 49 | 49 | 18 | 2130 | 7.2 |
| Example 8 | Fe = 0.4 | 0.8/9.8 | 46 | 45 | 8.9 | 310 | 9.9 |
| Example 9 | Fe = 0.04 | 1.7/11.2 | 43 | 42 | 6.9 | 220 | 8.5 |
| Example 10 | Cu = 0.4 | 2.1/8.7 | 49 | 47 | 10.9 | 620 | 10.0 |
| Example 11 | Mn = 0.4 | 4.2/14.0 | 42 | 43 | 6.3 | 360 | 11.0 |
| Example 12 | Ti = 0.4 | 2.0/13.2 | 42 | 42 | 6.5 | 260 | 11.0 |

Note):
In any water-absorbent resin, the weight-average particle diameter is in the range of about 430 to about 440 μm, and the quantity of fine particles having particle diameters of not larger than 150 μm is in the range of 2 to 5 wt %.

EXAMPLE 13

A quantity of 100 parts by weight of the water-absorbent resin powder (2), as obtained in Example 2, was spraywise mixed with a surface-crosslinking agent including glycerol 0.5/water 2/isopropanol 0.5 (weight ratio to the water-absorbent resin), and the resultant mixture was heat-treated at 210° C. for 35 minutes, thus obtaining a surface-crosslinked water-absorbent resin powder (13). The results are shown in Table 3.

EXAMPLES 14, 15

Surface-crosslinked water-absorbent resin powders (14) and (15) were obtained in the same ways as in Example 13 except that the water-absorbent resin powder (2) was replaced with the water-absorbent resin powder (3) or (4). The results are shown in Table 3.

TABLE 3

| | p-Methoxyphenol content (ppm by weight) | Absorption capacity without load GVj artificial urine (g/g) | Absorption capacity under load (4.9 kPa) (g/g) | SFC ($10^{-7} \times cm^3 \times s \times g^{-1}$) | Extractable content (wt %) | Residual monomer content (ppm by weight) | Coloring YI | Weight-average particle diameter D50 (μm) |
|---|---|---|---|---|---|---|---|---|
| Example 13 | 25 | 38 | 22 | 20 | 8.9 | 330 | 4.5 | 430 |
| Example 14 | 50 | 37 | 21 | 20 | 8.9 | 330 | 5 | 430 |
| Example 15 | 25 | 3.7. | 21 | 20 | 7.1 | 230 | 3.8 | 430 |
| Example 20 | 25 | 40 | 24 | 35 | 12 | 210 | 4.2 | 450 |
| Example 21 | 50 | 40 | 24 | 35 | 13 | 250 | 9.1 | 450 |
| Comparative Example 8 | 200 | 39 | 24 | 35 | 13 | 330 | 20.1 | 450 |

Note):
In any water-absorbent resin, the quantity of fine particles having particle diameters of not larger than 150 μm is in the range of 2 to 4 wt %.

Hereinafter set forth are further Examples and Comparative Examples as shown in Table 1 (polymerization) and Table 3 (surface-crosslinking).

EXAMPLE 16

Polymerization was carried out in the same way as in Example 2 except that, as the monomers, the acrylic acid composition (3) and the aqueous sodium acrylate solution (3) were replaced with the acrylic acid composition (5) (having a p-methoxyphenol content of 70 ppm by weight) and its neutralized product, namely, the aqueous sodium acrylate solution (5). Thereafter, the resultant polymer was dried and pulverized in the same way as in Example 2, and further then classified with a JIS standard sieve of 600 μm, thus obtaining a water-absorbent resin powder (16). The results are shown in Table 1.

EXAMPLE 17

Polymerization was carried out in the same way as in Example 2 except that, as the monomers, the acrylic acid composition (3) and the aqueous sodium acrylate solution (3) were replaced with an acrylic acid composition (11) (having a p-methoxyphenol content of 150 ppm by weight) and its neutralized product, namely, an aqueous sodium acrylate solution (11). Thereafter, the resultant polymer was dried and pulverized in the same way as in Example 2, and further then classified with a JIS standard sieve of 600 μm, thus obtaining a water-absorbent resin powder (17). The results are shown in Table 1.

Incidentally, the above acrylic acid composition (11) was obtained by adding p-methoxyphenol to the acrylic acid composition (1) (as obtained in Production Example 1) in a ratio of 150 ppm by weight (relative to solid content of acrylic acid). In addition, the aqueous sodium acrylate solution (11) was produced in accordance with Production Examples 8 to 11.

COMPARATIVE EXAMPLE 6

Polymerization was carried out in the same way as in Example 2 except that, as the monomers, the acrylic acid composition (3) and the aqueous sodium acrylate solution (3) were replaced with the acrylic acid composition (6) (having a p-methoxyphenol content of 200 ppm by weight) and its neutralized product, namely, the aqueous sodium acrylate solution (6). Thereafter, the resultant polymer was dried, pulverized, and classified in the same way as in Example 2, thus obtaining a comparative water-absorbent resin powder (6). The results are shown in Table 1.

EXAMPLE 18

A water-absorbent resin powder (18) was obtained in the same way as in Example 2 except that the aqueous monomer solution (2) was replaced with an aqueous monomer solution having a monomer concentration of 41 wt % and a neutralization ratio of 71 mol % as obtained by mixing together 537.4 g of the acrylic acid composition (3) (being obtained in Production Example 3 and having a p-methoxyphenol content of 25 ppm by weight) and 4,642.2 g of its neutralized product, namely, the aqueous sodium acrylate solution (3), and further, 312.3 g of ion-exchanged water, and polyethylene glycol diacrylate (molar-number-average degree "n" of addition polymerization of ethylene oxide=9) as an internal-crosslinking agent in an amount of 0.06 wt % (to the entire monomers). The results are shown in Table 1.

EXAMPLE 19

A water-absorbent resin powder (19) was obtained in the same way as in Example 18 except that the acrylic acid composition (3) and the aqueous sodium acrylate solution (3) were replaced with the acrylic acid composition (4) (being obtained in Production Example 4 and having a p-methoxyphenol content of 50 ppm by weight) and its neutralized product, namely, the aqueous sodium acrylate solution (4). The results are shown in Table 1.

COMPARATIVE EXAMPLE 7

A comparative water-absorbent resin powder (7) was obtained in the same way as in Example 18 except that, as the monomers, the acrylic acid composition (3) and the aqueous sodium acrylate solution (3) were replaced with the acrylic acid composition (6) (being obtained in Production Example 6 and having a p-methoxyphenol content of 200 ppm by weight) and its neutralized product, namely, the aqueous sodium acrylate solution (6). The results are shown in Table 1.

EXAMPLE 20

A quantity of 100 g of the water-absorbent resin powder (18), as obtained in Example 18, was mixed with a surface-crosslinking agent comprising a mixed solution of 0.384 g of 1,4-butanediol, 0.6 g of propylene glycol, 3.28 g of water, and 0.3 g (solid content=0.072 g) of 24 wt % aqueous sodium hydroxide solution, and the resultant mixture was heat-treated at 212° C. for 30 minutes, thus obtaining a surface-crosslinked water-absorbent resin powder (20). The results are shown in Table 3.

EXAMPLE 21

A surface-crosslinked water-absorbent resin powder (21) was obtained in the same way as in Example 20 except that the water-absorbent resin powder (18) was replaced with the water-absorbent resin powder (19) as obtained in Example 19. The results are shown in Table 3.

COMPARATIVE EXAMPLE 8

A comparative surface-crosslinked water-absorbent resin powder (8) was obtained in the same way as in Example 20 except that the water-absorbent resin powder (18) was replaced with the comparative water-absorbent resin powder (7) as obtained in Comparative Example 7. The results are shown in Table 3.

EXAMPLE 22

The acrylic acid composition (7) being obtained in Production Example 17 and having a p-methoxyphenol content of 55 ppm by weight was neutralized in accordance with Production Example 6 to obtain a 37 wt % aqueous sodium acrylate solution (7). Next, these acrylic acid composition (7) and 37 wt % aqueous sodium acrylate solution (7) were used to prepare 5,500 g of an aqueous sodium acrylate solution having a neutralization ratio of 75 mol % (monomer concentration=41 wt %, average molecular weight of monomer=88.55), into which polyethylene glycol diacrylate (molar-number-average degree "n" of addition polymerization of ethylene oxide=8) was then dissolved in an amount of 0.07 mol % (to the entire monomers), thus obtaining an aqueous monomer solution (22).

This aqueous monomer solution (22) was deaerated similarly in the same kneader reactor as used in Example 2. Subsequently, while the aqueous monomer solution (22) was similarly stirred at several tens of rpm, thereto there was added a polymerization initiator comprising a combination of an aqueous solution of sodium persulfate (in an amount of 0.12 g/mol) with an aqueous solution of L-ascorbic acid (in an amount of 0.001 g/mol). As a result, after about 1 minute, polymerization started. Then, while the resultant gel was stirred and disintegrated, the polymerization was carried out in the range of 20 to 95° C., and then, after 30 minutes from the start of the polymerization, there was got out a finely-disintegrated crosslinked hydrogel polymer (22) having particle diameters in the range of about 1 to about 2 mm. Next, this polymer was spread onto a metal gauze of 300 μm in mesh opening size and then hot-wind-dried at 180° C. for 40 minutes. The resultant dried product was pulverized with a roller mill, and further then classified with JIS standard sieves of 600 μm and 300 μm respectively in mesh opening size, thus obtaining a water-absorbent resin powder (22) of which most of the particles had particle diameters in the range of 600 to 300 μm.

A quantity of 100 g of the resultant water-absorbent resin powder (22) was mixed with a surface-crosslinking agent comprising a mixed solution of 0.384 g of 1,4-butanediol, 0.6 g of propylene glycol, 3.28 g of water, and 0.3 g (solid content=0.072 g) of 24 wt % aqueous sodium hydroxide solution, and the resultant mixture was heat-treated at 212° C. for 40 minutes, thus obtaining a surface-crosslinked water-absorbent resin powder (22).

EXAMPLE 23

Influences of Hydrogen Peroxide:

Polymerization was carried out in the same way as in Example 22 except that, as the polymerization initiators, an aqueous solution of hydrogen peroxide (in an amount of 0.000432 g/mol) was also added besides the aqueous solution of sodium persulfate (in an amount of 0.12 g/mol) and the aqueous solution of L-ascorbic acid (in an amount of 0.001 g/mol). Thereafter, the resultant polymer was dried, pulverized, classified, and surface-crosslinked in the same way as in Example 22, thus obtaining a surface-crosslinked water-absorbent resin powder (23).

EXAMPLE 24

Increase of Quantity of Hydrogen Peroxide

Polymerization was carried out in the same way as in Example 23 except that the quantity of the hydrogen peroxide as added was increased to 0.003 g/mol. Thereafter, the resultant polymer was dried, pulverized, classified, and surface-crosslinked in the same way as in Example 23, thus obtaining a surface-crosslinked water-absorbent resin powder (24).

EXAMPLE 25

Increase of Quantity of Sodium Persulfate:

Polymerization was carried out in the same way as in Example 22 except that the quantity of the sodium persulfate as added was increased to 0.13 g/mol. Thereafter, the resultant polymer was dried, pulverized, classified, and surface-crosslinked in the same way as in Example 22, thus obtaining a surface-crosslinked water-absorbent resin powder (25).

EXAMPLE 26

Influences of Neutralization Ratio (change from 75 mol % to 71.3 mol %):

An aqueous monomer solution (26) having a neutralization ratio of 71.3 mol % was prepared in the same way as in Example 25 except that polyethylene glycol diacrylate (molar-number-average degree "n" of addition polymerization of ethylene oxide=9) was dissolved in an amount of 0.07 mol % (to the entire monomers). Thereafter, in the same way as in Example 25, the aqueous monomer solution (26) was polymerized, and the resultant polymer was dried, pulverized, classified, and surface-crosslinked, thus obtaining a surface-crosslinked water-absorbent resin powder (26). Incidentally, by this reduction of the neutralization ratio, the reaction time of the surface-crosslinking could be shortened a little when compared with that in Example 25.

EXAMPLE 27

Change of Neutralization Ratio into 65 mol %:

An aqueous monomer solution (27) having a neutralization ratio of 65 mol % was prepared in the same way as in Example 25 except that polyethylene glycol diacrylate (molar-number-average degree "n" of addition polymerization of ethylene oxide=9) was dissolved in an amount of 0.07 mol % (to the entire monomers). Thereafter, in the same way as in Example 25, the aqueous monomer solution (27) was polymerized, and the resultant polymer was dried, pulverized, classified, and surface-crosslinked, thus obtaining a surface-crosslinked water-absorbent resin powder (27). Incidentally, by this reduction of the neutralization ratio, the reaction time of the surface-crosslinking could be shortened more than in Example 26.

The results of Examples 22 to 27 are shown in Table 4.

TABLE 4

|  | Example 22 | Example 23 | Example 24 | Example 25 | Example 26 | Example 27 |
| --- | --- | --- | --- | --- | --- | --- |
| Neutralization ratio (mol %) | 75 | 75 | 75 | 75 | 71.3 | 65 |
| Sodium persulfate (g/mol) | 0.12 | 0.12 | 0.12 | 0.13 | 0.13 | 0.13 |
| Hydrogen peroxide (g/mol) | 0 | 0.000432 | 0.003 | 0 | 0 | 0 |
| Absorption capacity without load GVj (artificial urine) (g/g) | 40 | 40 | 40 | 41 | 40 | 40 |

TABLE 4-continued

|  | Example 22 | Example 23 | Example 24 | Example 25 | Example 26 | Example 27 |
|---|---|---|---|---|---|---|
| Absorption capacity under load (4.9 kPa) (g/g) | 26 | 26 | 26 | 26 | 25 | 25 |
| SFC ($10^{-7} \times cm^3 \times s \times g^{-1}$) | 40 | 40 | 40 | 40 | 40 | 40 |
| Color difference |  |  |  |  |  |  |
| L | 88.1 | 88.8 | 89.1 | 88.0 | 89.3 | 89.8 |
| a | −0.41 | −0.59 | −0.65 | −0.57 | −0.74 | −0.6 |
| b | 6.29 | 6.28 | 6.09 | 6.71 | 6.8 | 5.9 |
| YI | 12.63 | 12.38 | 11.9 | 13.36 | 13.23 | 11.46 |
| Hunter Color (WB) | 69.9 | 71.0 | 71.8 | 69.2 | 71.2 | 73.3 |

EXAMPLE 28

Influences of Protoanemonin:

An aqueous monomer solution (28) was obtained from the acrylic acid composition (10) (having a protoanemonin content of 30 ppm by weight in addition to a p-methoxyphenol content of 50 ppm by weight) and its neutralized product (obtained by neutralization according to Production Example 6) in the same way as in Example 3. From the resultant aqueous monomer solution (28) having a protoanemonin content of 30 ppm by weight (relative to solid content of acrylic acid), a water-absorbent resin powder (28) was obtained by carrying out the polymerization, drying, pulverization, and classification in the same way as in Example 3. In comparison of the resultant water-absorbent resin powder (28) with the water-absorbent resin powder (3) of Example 3 having a protoanemonin content of ND, the polymerization rate (peak time) extended by about 5 minutes, and the extractable content increased by 2 wt %, and the residual monomer content also increased by 200 ppm by weight.

EXAMPLE 29

Influences of Time After Neutralization:

An aqueous monomer solution (29) was obtained in the same way as in Example 2 except that the aqueous sodium acrylate solution (3) was not used until being left alone for 72 hours after the neutralization. From the resultant aqueous monomer solution (29), a water-absorbent resin powder (29) was obtained by carrying out the polymerization, drying, pulverization, and classification in the same way as in Example 2. In comparison of the resultant water-absorbent resin powder (29) with the water-absorbent resin powder (2) of Example 2 (in which the aqueous sodium acrylate solution was used for the preparation of the aqueous monomer solution within 30 minutes after the neutralization), the YI deteriorated by 1.0, and the residual monomer content also increased by 200 ppm by weight.

EXAMPLE 30

Influences of Time of Till Start of Drying:

A water-absorbent resin powder (30) was obtained by carrying out the polymerization, drying, pulverization, and classification in the same way as in Example 2 except that the time of from obtaining the crosslinked hydrogel polymer (2) until starting to dry it was changed to 2 hours. In comparison of the resultant water-absorbent resin powder (30) with the water-absorbent resin powder (2) of Example 2 (in which the drying of the crosslinked hydrogel polymer was started immediately after it had been obtained), the YI deteriorated by 1.0, and the residual monomer content also increased by 20 ppm by weight.

As is understood from Table 1, the time as needed until the polymerization reaches its peak is shorter (in other words, the polymerization rate is also higher) when p-methoxyphenol is allowed to coexist in a quantity of 10–160 ppm by weight during the polymerization than when the polymerization is carried out under conditions where p-methoxyphenol is contained in a quantity of 200 ppm by weight or has entirely been removed. Further from comparison of Example 1 with Comparative Examples 2,3 and from comparison of Examples 2, 3 with Comparative Example 3, it is also understood that, if p-methoxyphenol is used in a quantity of 10–160 ppm by weight, then the water absorption capacity and the extractable content also become better (the absorption capacity increases and the water-extractable content decreases).

Incidentally, though not being shown in Table 1, the comparative aqueous monomer solutions (1), (3), and (4) do not contain any p-methoxyphenol, therefore they are inferior in preservation stability and, in the case where left alone for a long time or deaerated, they displayed partial polymerization before a polymerization initiator was added thereto. Furthermore, the water-absorbent resin of Comparative Example 2, as obtained by using the p-methoxyphenol in a quantity of 200 ppm by weight, was somewhat of a yellow tinge when compared with that of Example 1 as obtained by using the p-methoxyphenol in a quantity of 20 ppm by weight. Specifically, the water-absorbent resin according to the present invention exhibits a YI value (Yellow Index) favorably in the range of 0 to 15, particularly favorably 0 to 5, and has no tinge of yellow and is white.

As is understood from Table 2, if a transition metal is allowed to coexist in the specific quantity (favorably in the range of 0.2 to 1 ppm by weight) during the polymerization, the polymerization rate becomes higher, and so do the properties.

As is understood from Table 3, the excellent surface-crosslinking effects are displayed. In addition, the water-absorbent resins according to the present invention, obtained by surface-crosslinking as shown in Table 3, display an absorption capacity of not less than 20 g/g under a load and/or a saline flow conductivity of not less than 20 ×$10^{-7}$ ($cm^3 \cdot s \cdot g^{-1}$), and further, have also achieved the aforementioned object of the present invention (which is to produce inexpensively with high productivity a water-absorbent resin of which the residual monomer content and the water-extractable content are both low, and the properties are high, and the colorability is low). Although favorable ranges of these parameters are aforementioned, such water-absorbent resins have a residual monomer content of favorably not more than 300 ppm by weight and also exhibit a YI value favorably in the range of 0 to 5.

As is understood from Table 4, even if the p-methoxyphenol content is the same (55 ppm by weight), either the use of hydrogen peroxide in the polymerization or the reduction of the neutralization ratio of the monomers provides still better results with regard to the low colorability of the resultant water-absorbent resin with its high properties kept.

In FIG. 1, variations in polymerization with the passage of time in Example 1 and Comparative Examples 1 and 2 are shown by reaction temperature (temperature of monomer or hydrogel in progress of the polymerization/proportional to generation of heat of the polymerization).

Though being evident also from FIG. 1, it is understood that the polymerization rate is also much higher when the aqueous monomer solution is polymerized under conditions where p-methoxyphenol is present in a quantity of 10 to 160 ppm by weight than when the polymerization is carried out under conditions where p-methoxyphenol is used in a quantity of 200 ppm by weight (Comparative Example 2) or ND (less than 1 ppm by weight) as a result of entire removal of p-methoxyphenol (Comparative Example 1).

Further shown in Table 1 are the residual monomer contents of the hydrogels as obtained by polymerization in Example 1 and Comparative Examples 1 and 2. After polymerization, the residual monomer content in Example 1 is 1.6 wt % in comparison with 7.0 wt % in Comparative Example 1 and 3.3 wt % in Comparative Example 2. Thus, the polymerization conversion is also greatly enhanced if the aqueous monomer solution is polymerized under conditions where p-methoxyphenol is present in a quantity of 10 to 160 ppm by weight.

In addition, though not being shown in Table 1, yet in comparisons between Examples 2 and 4 and between Examples 3 and 5 (in each comparison, the p-methoxyphenol content is the same), the treatment with active carbon in Examples 4 and 5 enhanced both the light resistance (the deteriorated extractable content of about 30 wt % reduced to about 15 wt %) and the urine resistance (neither deterioration nor movement of the gel was seen with the eye) and further the gel strength.

INDUSTRIAL APPLICATION

The water-absorbent resin of high properties can be obtained at a fast polymerization rate by: the process for producing a crosslinked water-absorbent resin by polymerizing a monomer component including acrylic acid and/or its salt in a major proportion; and the use of the acrylic acid composition suitable for this process. That is to say, there has been achieved the aforementioned object of the present invention (which is to produce inexpensively with high productivity a water-absorbent resin of which the residual monomer content and the water-extractable content are both low, and the properties are high, and the coloring is low).

The invention claimed is:

1. A process for producing a water-absorbent resin, which is a process for producing a crosslinked water-absorbent resin by polymerizing a monomer component including acrylic acid and/or its salt in a major proportion of the monomer component wherein the acrylic acid is a product obtained by catalytic gas phase oxidation of propylene and/or propane,
with the process being characterized by comprising the steps of: preparing the monomer component from an acrylic acid composition that includes the unneutralized acrylic acid and a methoxyphenol and has a methoxyphenol content of 10 to 160 ppm by weight (based on the weight of the unneutralized acrylic acid); and then carrying out radical and/or ultraviolet polymerization of the resultant monomer component.

2. A process for producing a water-absorbent resin, which is a process for producing a crosslinked water-absorbent resin by polymerizing a monomer component including acrylic acid and/or its salt in a major proportion wherein the acrylic acid is a product obtained by catalytic gas phase oxidation of propylene and/or propane,
the process being characterized by comprising the steps of: preparing the monomer component from an acrylic acid composition that includes the unneutralized acrylic acid; and then carrying out radical and/or ultraviolet polymerization of the resultant monomer component in the presence of a methoxyphenol in an amount of 10 to 160 ppm by weight relative to the weight of acrylic acid and/or its salt (based on the weight in terms of the unneutralized acrylic acid) in the monomer component.

3. A process for producing a water-absorbent resin, which is a process for producing a crosslinked water-absorbent resin by polymerizing a monomer component including acrylic acid and/or its salt in a major proportion wherein the acrylic acid is a product obtained by catalytic gas phase oxidation of propylene and/or propane,
the process being characterized by comprising the steps of: treating an acrylic acid composition and/or its neutralized product with an adsorbing agent wherein the acrylic acid composition includes the unneutralized acrylic acid and a methoxyphenol; and then preparing the monomer component from the resultant acrylic acid product; and then carrying out radical and/or ultraviolet polymerization of the resultant monomer component.

4. A process according to claim 1, wherein the step of carrying out the radical and/or ultraviolet polymerization is carried out in the presence of a transition metal ion.

5. A process according to claim 2, wherein the step of carrying out the radical and/or ultraviolet polymerization is carried out in the presence of a transition metal ion.

6. A process according to claim 3, wherein the step of carrying out the radical and/or ultraviolet polymerization is carried out in the presence of a transition metal ion.

7. A process according to claim 4, wherein the monomer component has a transition metal ion content of 0.1 to 2 ppm by weight in terms of transition metal.

8. A process according to claim 1, wherein the acrylic acid composition has a protoanemonin and/or furfural content of not more than 20 ppm by weight (relative to the monomers).

9. A process according to claim 2, wherein the acrylic acid composition has a protoanemonin and/or furfural content of not more than 20 ppm by weight (relative to the monomers).

10. A process according to claim 3, wherein the acrylic acid composition has a protoanemonin and/or furfural content of not more than 20 ppm by weight (relative to the monomers).

11. A process according to claim 1, further comprising the step of crosslinking surfaces of the resultant resin and their neighborhoods.

12. A process according to claim 2, further comprising the step of crosslinking surfaces of the resultant resin and their neighborhoods.

13. A process according to claim 3, further comprising the step of crosslinking surfaces of the resultant resin and their neighborhoods.

14. A process according to claim 1, involving use of a polymerization initiator including hydrogen peroxide.

15. A process according to claim 2, involving use of a polymerization initiator including hydrogen peroxide.

16. A process according to claim 3, involving use of a polymerization initiator including hydrogen peroxide.

17. A process according to claim 1, wherein the monomer component has a neutralization ratio of not more than 75 mol %.

18. A process according to claim 2, wherein the monomer component has a neutralization ratio of not more than 75 mol %.

19. A process according to claim 3, wherein the monomer component has a neutralization ratio of not more than 75 mol %.

20. A process according to claim 1, wherein the polymerization is initiated within 24 hours after the preparation of the monomer component and/or neutralization of the acrylic acid.

21. A process according to claim 1, wherein the polymerization is initiated within 24 hours after the preparation of the monomer component and/or neutralization of the acrylic acid.

22. A process according to claim 3, wherein the polymerization is initiated within 24 hours after the preparation of the monomer component and/or neutralization of the acrylic acid.

23. A process according to claim 1, further comprising the steps of, within 1 hour after the polymerization, starting to dry the resultant polymer; and then forming a powder having a weight-average particle diameter in the range of 300 to 500 μm wherein the quantity of particles having particle diameters in the range of 850 to 150 μm is not less than 90 wt %.

24. A process according to claim 2, further comprising the steps of, within 1 hour after the polymerization, starting to dry the resultant polymer; and then forming a powder having a weight-average particle diameter in the range of 300 to 500 μm wherein the quantity of particles having particle diameters in the range of 850 to 150 μm is not less than 90 wt %.

25. A process according to claim 3, further comprising the steps of, within 1 hour after the polymerization, starting to dry the resultant polymer; and then forming a powder having a weight-average particle diameter in the range of 300 to 500 μm wherein the quantity of particles having particle diameters in the range of 850 to 150 μm is not less than 90 wt %.

26. A process according to claim 1, wherein the unneutralized acrylic acid being used has a methoxyphenol content of 10 to 160 ppm by weight and is a product obtained by treating the acrylic acid by distillation and/or crystallization.

27. A process according to claim 2, wherein the unneutralized acrylic acid being used has a methoxyphenol content of 10 to 160 ppm by weight and is a product obtained by treating the acrylic acid by distillation and/or crystallization.

28. A process according to claim 3, wherein the unneutralized acrylic acid being used has a methoxyphenol content of 10 to 160 ppm by weight and is a product obtained by treating the acrylic acid by distillation and/or crystallization.

29. A process according to claim 1, wherein the methoxyphenol is p-methoxyphenol.

30. A process according to claim 2, wherein the methoxyphenol is p-methoxyphenol.

31. A process according to claim 3, wherein the methoxyphenol is p-methoxyphenol.

32. A water-absorbent resin, being a product obtained by the process as recited in claim 1,
with the water-absorbent resin displaying an absorption capacity of not less than 20 g/g under a load and/or a saline flow conductivity of not less than $20 \times 10^{-7}$ ($cm^3 \cdot s \cdot g^{-1}$).

33. A water-absorbent resin, being a product obtained by the process as recited in claim 2,
with the water-absorbent resin displaying an absorption capacity of not less than 20 g/g under a load and/or a saline flow conductivity of not less than $20 \times 10^{-7}$ ($cm^3 \cdot s \cdot g^{-1}$).

34. A water-absorbent resin, being a product obtained by the process as recited in claim 3,
with the water-absorbent resin displaying an absorption capacity of not less than 20 g/g under a load and/or a saline flow conductivity of not less than $20 \times 10^{-7}$ ($cm^3 \cdot s \cdot g^{-1}$).

35. A sanitary material, comprising the water-absorbent resin as recited in claim 32.

36. A sanitary material, comprising the water-absorbent resin as recited in claim 33.

37. A sanitary material, comprising the water-absorbent resin as recited in claim 34.

38. An acrylic acid composition, comprising unneutralized acrylic acid and being used in producing a crosslinked water-absorbent resin by polymerizing a monomer component including acrylic acid and/or its salt in a major proportion wherein the acrylic acid is a product obtained by catalytic gas phase oxidation of propylene and/or propane,
with the acrylic acid composition being characterized by having a protoanemonin and/or furfural content of not more than 20 ppm by weight (relative to the unneutralized acrylic acid) and a methoxyphenol content of 10 to 160 ppm by weight relative to the unneutralized acrylic acid.

39. A process for producing an acrylic acid composition, which is a process for producing an acrylic acid composition comprising unneutralized acrylic acid and being used in producing a crosslinked water-absorbent resin by polymerizing a monomer component including acrylic acid and/or its salt in a major proportion wherein the acrylic acid is a product obtained by catalytic gas phase oxidation of propylene and/or propane,
with the process being characterized by comprising the step of carrying out treatment of methoxyphenol-containing acrylic acid by distillation and/or crystallization to adjust its methoxyphenol content into the range of 10 to 160 ppm by weight relative to the unneutralized acrylic acid.

40. A process according to claim 1, wherein the methoxyphenol content is 10 to 90 ppm by weight based on the weight of the unneutralized acrylic acid.

41. A process according to claim 1, wherein the methoxyphenol content is 20 to 140 ppm by weight based on the weight of the unneutralized acrylic acid.

42. A process according to claim 1, wherein the methoxyphenol content is 50 to 90 ppm by weight based on the weight of the unneutralized acrylic acid.

43. A process according to claim 3, wherein said adsorbing agent is active carbon.

44. A process according to claim 1, wherein said water-absorbent resin has a yellowing index of 0 to 15.

45. A process according to claim 1, wherein said methoxyphenol is included in an effective amount to promote a rate of said polymerization.

46. A process according to claim 2, wherein said water-absorbent resin has a yellowing index of 0 to 15.

47. A process according to claim 3, wherein said water-absorbent resin has a yellowing index of 0 to 15.

* * * * *